United States Patent [19]
Lapeus et al.

[11] Patent Number: 5,720,377
[45] Date of Patent: Feb. 24, 1998

[54] MAGNETIC CONVEYOR SYSTEM

[75] Inventors: David J. Lapeus, Garfield Heights; Michael Ballash, Lakewood, both of Ohio

[73] Assignee: Chiron Diagnostics Corporation, E. Walpole, Mass.

[21] Appl. No.: 502,653

[22] Filed: Jul. 14, 1995

[51] Int. Cl.$^6$ .................................................. B65G 37/00
[52] U.S. Cl. ..................... 198/346.1; 198/465.1; 198/619; 198/803.01
[58] Field of Search ............................. 198/346.1, 346.2, 198/465.1, 465.2, 619, 803.01, 341

[56] References Cited

U.S. PATENT DOCUMENTS

| | | | |
|---|---|---|---|
| 2,609,915 | 9/1952 | DeBurgh | 198/42 |
| 2,824,638 | 2/1958 | DeBurgh | 198/41 |
| 3,474,892 | 10/1969 | Spodig | 198/619 |
| 4,040,533 | 8/1977 | DeBoer et al. | 198/465.2 |
| 4,059,185 | 11/1977 | Weber | 198/346.2 |
| 4,088,254 | 5/1978 | Hooper | 224/45 R |
| 4,228,831 | 10/1980 | Kerns | 141/27 |
| 4,413,534 | 11/1983 | Tomoff et al. | 732/864.21 |
| 4,438,068 | 3/1984 | Forrest | 422/61 |
| 4,439,700 | 3/1984 | Menzel et al. | 310/13 |
| 4,454,939 | 6/1984 | Kampf et al. | 198/346.1 |
| 4,503,964 | 3/1985 | Kampf et al. | 198/341 |
| 4,506,777 | 3/1985 | Kampf | 198/465.2 |
| 4,526,754 | 7/1985 | Burns et al. | 422/82 |
| 4,528,159 | 7/1985 | Liston | 422/65 |
| 4,609,017 | 9/1986 | Coulter et al. | 141/1 |
| 4,678,752 | 7/1987 | Thorne et al. | 435/291 |
| 4,736,748 | 4/1988 | Nakamura et al. | 128/632 |
| 4,751,184 | 6/1988 | Higo et al. | 435/287 |
| 4,751,186 | 6/1988 | Baisch et al. | 436/47 |

(List continued on next page.)

FOREIGN PATENT DOCUMENTS

| | | | |
|---|---|---|---|
| 0565166 | 10/1993 | European Pat. Off. | G01N 35/04 |
| 5264413 | 10/1993 | Japan | G01N 1/00 |

OTHER PUBLICATIONS

"1.3 Sample Transport System," *Boehringer Mannheim/Hitachi 747–100 Analyzer Operator's Manual*, vol. 1, pp. 1–15 to 1–20 (1992).

"5.4 Sample Transport System," *Boehringer Mannheim/Hitachi 747–100 Analyzer Operator's Manual*, vol. 2, pp. 5–13 to 5–24 (1992).

rosys Plato 3300, Rosys, Inc. catalog (not dated—obtained by Applicants Aug. 1994).

"Section 19—Primary Container Sampling," *Kodak Ektachem MP2–52 Manual*, Nov. 1987.

*Primary Examiner*—Joseph E. Valenza
*Attorney, Agent, or Firm*—Arthur S. Morgenstern; Charles Gagnebin, III; Robert P. Blackburn

[57] ABSTRACT

A magnetic conveyor system for transporting test samples in tubes disposed in a sample rack having a magnetic or magnetically attractive region is described. The magnetic conveyor system includes a drive system, a magnet coupled to the drive system and movable in response to the drive system and a tray having a first surface adapted to receive the sample rack. The magnet is spaced a predetermined distance from the first surface of the tray such that the magnet provides a magnetic force at the surface of the tray. The magnetic force engages the magnetically attractive region of the sample rack disposed on the tray to thereby move the sample rack along the first surface of the tray in response to movement of the drive system. When the tray reaches the end of the rack it is moved onto a processing queue tray where it is available for test purposes. A barcode reader reads a bar code on each test sample as it is placed on the process queue to identify one or more tests to perform. When all samples have received the individual tests the rack exits to an output queue for disposal. When a test must be made on an immediate basis out of normal processing order a sample rack can be inserted into the process queue via a priority rack feed. In the indicated manner, testing can continue without interruption as new racks are added and completed racks removed.

16 Claims, 24 Drawing Sheets

U.S. PATENT DOCUMENTS

| | | | |
|---|---|---|---|
| 4,861,553 | 8/1989 | Mawhirt et al. | 422/65 |
| 4,861,554 | 8/1989 | Sakuma | 422/65 |
| 4,896,064 | 1/1990 | Taiani | 310/104 |
| 4,900,513 | 2/1990 | Barker et al. | 422/64 |
| 4,943,416 | 7/1990 | Kikuchi et al. | 422/63 |
| 4,944,924 | 7/1990 | Mawhirt et al. | 422/104 |
| 4,953,684 | 9/1990 | Beswick | 198/311 |
| 4,956,148 | 9/1990 | Grandone | 422/64 |
| 4,964,839 | 10/1990 | Gloor | 464/29 |
| 4,981,208 | 1/1991 | Jones | 198/778 |
| 4,994,240 | 2/1991 | Hayashi | 422/63 |
| 5,008,082 | 4/1991 | Shaw | 422/65 |
| 5,012,669 | 5/1991 | Meyer | 73/25.02 |
| 5,035,861 | 7/1991 | Grandone | 422/64 |
| 5,055,262 | 10/1991 | Sakagami | 422/64 |
| 5,059,393 | 10/1991 | Quenin et al. | 422/64 |
| 5,089,424 | 2/1992 | Khalil et al. | 436/518 |
| 5,104,808 | 4/1992 | Laska et al. | 436/48 |
| 5,128,105 | 7/1992 | Berthold et al. | 422/104 |
| 5,178,834 | 1/1993 | Kagayama et al. | 422/65 |
| 5,205,396 | 4/1993 | Grecksch et al. | 198/465.1 |
| 5,244,633 | 9/1993 | Jakubowicz et al. | 422/64 |
| 5,286,651 | 2/1994 | Smith | 436/32 |
| 5,311,426 | 5/1994 | Donohue et al. | 364/413.09 |
| 5,320,808 | 6/1994 | Holen et al. | 422/64 |
| 5,324,481 | 6/1994 | Dunn et al. | 422/64 |
| 5,366,697 | 11/1994 | Tomasso et al. | 422/64 |

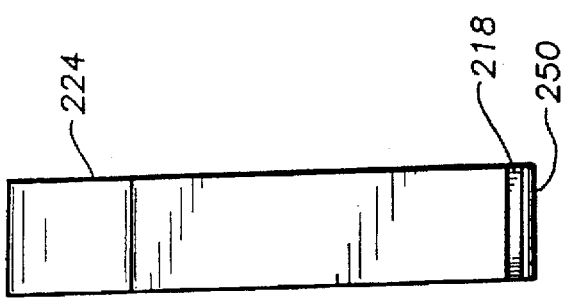
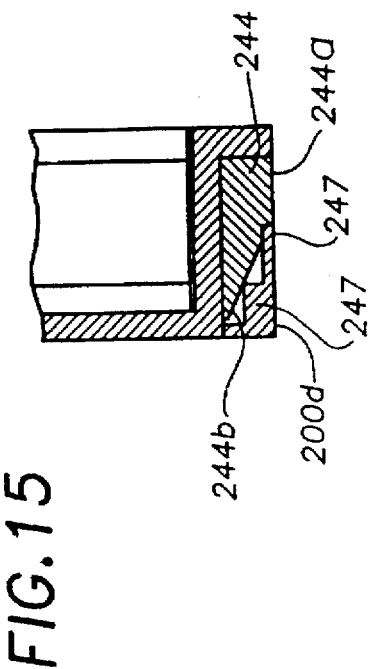
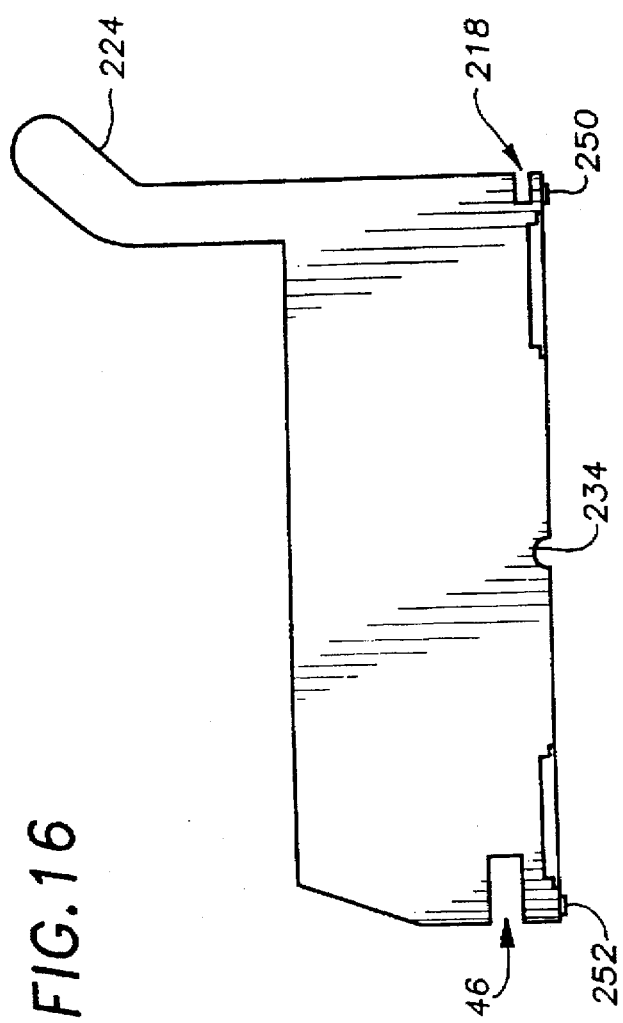

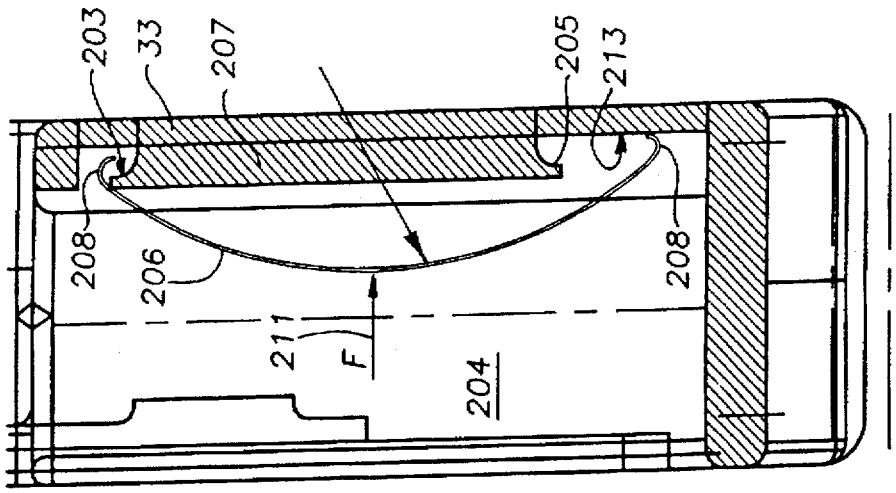
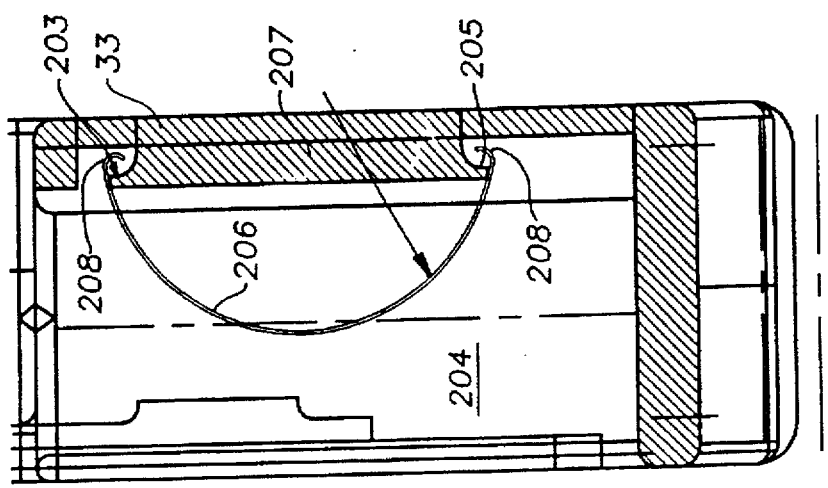
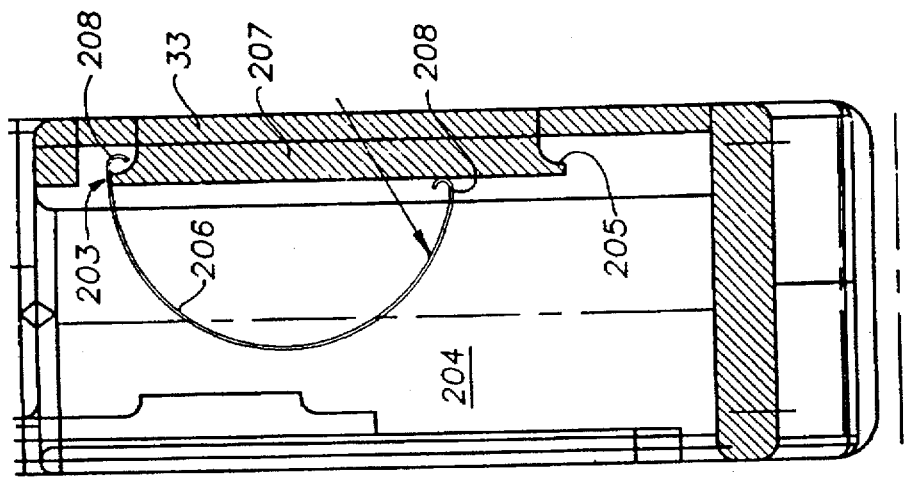

5,720,377

MAGNETIC CONVEYOR SYSTEM

FIELD OF THE INVENTION

This invention relates to analyzer instruments and more particularly to systems for moving test samples into and out of an analyzer instrument.

BACKGROUND OF THE INVENTION

As is known in the art, there is a trend in hospitals, clinics, laboratories and other locations to perform tests (assays) on samples of patient specimens such as blood, spinal fluid, urine, serum, plasma, and the like using automated analyzer systems. The samples are typically placed in a container such as a sample cup, a primary tube, a cuvette or any other suitable container. One or more of such containers may then be arranged in a so-called sample rack.

The sample rack is placed in a load area or input queue of the analyzer instrument and then is moved to a position where at least a portion of the sample is collected for testing in the analyzer instrument. After the sample is collected for testing in the analyzer instrument, the sample rack is moved to an output or exit queue where the user can remove the sample rack from the analyzer instrument. Thus, a user can physically place sample racks holding one or more samples to be tested in the load area and after the samples are collected the user can remove the sample racks from the output queue. Thus, the entry and exit queues of the analyzer instrument are generally exposed to a user.

In a typical analyzer instrument, mechanical pushers or conveyor mechanisms are used to moved the sample racks along the input and output queues. In the mechanical pusher approach, a pusher apparatus is positioned above a tray on which the sample racks are disposed. A lead screw driven by a motor or a spring driven push block pushes the sample racks along a surface of the tray.

When such mechanical pushers are used in input and output sample queues where user interaction is high, special precautions generally must be taken to insure safe operation. For example, safety shields and safety guides are generally used to cover the mechanical pusher to thus prevent a user from being harmed by moving parts to which the user would otherwise be exposed. Such precautions lead to the mechanical pusher having additional parts which in turn leads to a relatively complex design.

Moreover, the input and output queues are generally susceptible to sample fluid spills and thus it is important to allow the queues to be easily cleaned. The above mentioned safety precautions, however, limit user accessibility to the tray. Furthermore, due to the likelihood of the user being harmed by a moving machinery, it is undesirable for a user to attempt to clean the tray while the pusher apparatus is operating. Thus, the pusher apparatus is preferably stopped to allow the user to clean the input and exit queues in the regions proximate the pusher mechanisms. This usually slows or stops operation of the system.

Furthermore, any openings in the surface of the input and output trays upon which the sample racks are placed may expose interior portions of the transport system or analyzer instrument to fluid spills. Such interior areas are generally not easily accessible and if such areas become contaminated by fluid, further complications arise in the cleaning procedures.

Conveyer type mechanisms have similar problems. In the conveyor approach, a sample rack is placed on a belt which continuously moves around two or more wheels or pulleys. If a fluid sample spills onto the moving belt, the belt carries the fluid to interior areas of the conveyor system thereby possibly contaminating inner portions of the conveyor system or analyzer instrument.

An additional concern in the conveyor approach is that the sample racks are moved to one end of either the input or exit queues and come to rest against a rack stop. The conveyor belt, however, must continuously slide under the racks which have collected and rest in a fixed position at the end of the queue. This may lead to considerable wear on the belt as well as on the bottom surface of the sample racks which are stationary at the end of the queue.

It would thus be desirable to provide a sample transport system which moves sample racks along a transport tray while minimizing the risk of injury to a user, maximizes user accessibility to test samples on input and exit queues and minimizes the amount of effort required to clean input and exit queues.

SUMMARY OF THE INVENTION

In accordance with the present invention, a transport system for moving a sample rack having a magnetically attractive region includes a drive system, a magnet coupled to the drive system and movable in response to the drive system and a tray having a first surface adapted to receive the sample rack wherein the first surface of the tray is disposed over and spaced a predetermined distance from a first surface of the magnet such that a magnetic force provided by the magnet is present at the first surface of the tray. With this particular arrangement, a magnetic conveyor system is provided. By disposing the tray over the drive system, the drive mechanism is completely isolated from the user thus minimizing safety hazards. Furthermore, since the sample racks are magnetically coupled to the drive system, the surface of the tray need not move or contain any slots or particular indexing regions. Thus in the event of a fluid spill, the fluid is prevented from contaminating internal regions of the transport system and analyzer system. Furthermore, the tray may be provided from a material which promotes cleaning thereby enabling the tray to be easily cleaned. For example, the tray may be fabricated of aluminum having a Teflon surface coating. Also, the tray can be coupled to a cover which completely encloses the drive system and further protects the drive system from sample spills and other contaminants. Moreover, the tray surface upon which racks are disposed is stationary and thus does not cause excessive wear of the sample racks due to constant rubbing of a moving belt on the bottom surface of a stationary sample rack. Furthermore, there are no moving parts to which a user is exposed and thus the transport system minimizes the safety concerns of a user in highly accessible areas such as an input queue of an analyzer instrument.

The tray is provided having a rectangular shape with a length selected to hold a predetermined number of sample racks. In one embodiment, each sample rack holds one or more test tubes. The sample racks may be loaded onto any portion of the tray which serves as an input queue of the analyzer instrument. The drive system located beneath the first surface of the tray includes a first shaft disposed below a first end of the tray and a second shaft disposed below a second different end of the tray. The shafts are rotatably mounted in a base. Each shaft has a pair of pulleys disposed on opposite ends thereto. A urethane belt is disposed around opposing pulleys of the two shafts. A plurality of bar magnet assemblies extend between the urethane belts. The pulley sets synchronously drive the two urethane belts and thus the magnet assemblies. The magnet assemblies include a pair of magnets oriented such that opposite poles of each magnet face the same tray surface forming a magnet circuit which includes a magnetic field above the first surface of the tray. The magnet assemblies and the first surface of the tray are closely spaced such that the magnets freely move with the urethane belts below the surface of the tray.

In one embodiment, each sample rack is provided having two cavities on a bottom surface thereof. The cavities are symmetrically located about opposite sides of a center line of the sample rack. Disposed in each of the cavities is a magnetizable plate positioned at the bottom surface of the sample rack such that when the sample rack is disposed on the tray the plates are aligned with the magnets of the magnet assemblies which pass below the surface of the tray. The magnetic field generated by the magnet assemblies attract the plates disposed in the bottom surface of the sample rack and engages the plate with sufficient force such that the sample rack moves in concert with the magnet assembly as the belts move. At least a portion of a first surface of the plate may be disposed at an angle with respect to the surface of the magnet assembly such that the magnetic force provided by the magnet assemblies gradually builds as the belts move to lower the backward acceleration of the rack as the magnet assembly first approaches the sample rack. Consequently, the sample rack smoothly transitions from a stationary state to a moving state.

The sample rack is also provided having a pair of rails projecting from the bottom surface thereof. The rails decrease the surface area of the sample rack which contact the tray and thus reduce frictional forces between the sample rack and the tray. The bottom surface of the sample rack is also provided with a recess region which accepts projecting guide from the first surface of the tray. The guide positions the sample rack along the tray. The sample rack also includes front and back edge guides which prevent the sample rack from tipping while it is on the tray and ensures that the rack is properly aligned on the tray. The front edge guide prevents the sample rack from tipping when the sample rack is placed in a load position of the tray.

The sample rack has openings to accept sample-containing vessels such as test tubes. Disposed on each of the openings is a finger spring which is placed in compression when a sample-containing vessel is placed in the opening, thus securing the sample vessel in the sample rack. The spring is sized such that different size test tubes may be placed and properly secured in the sample rack.

BRIEF DESCRIPTION OF THE DRAWINGS

The foregoing features of this invention as well as the invention itself may be more fully understood from the following detailed description of the drawings in which

FIGS. 5A and 5B show alternative details of FIG. 5;

FIG. 15 is a side view of a sample rack;

FIG. 16 is a cross sectional view of a portion of a magnetic sample rack;

FIG. 17 is an end view of a sample rack; and

FIGS. 18A–18C are a cross sectional view of a sample rack slot showing installation and compression of a spring.

DESCRIPTION OF THE PREFERRED EMBODIMENTS

Figure 1:
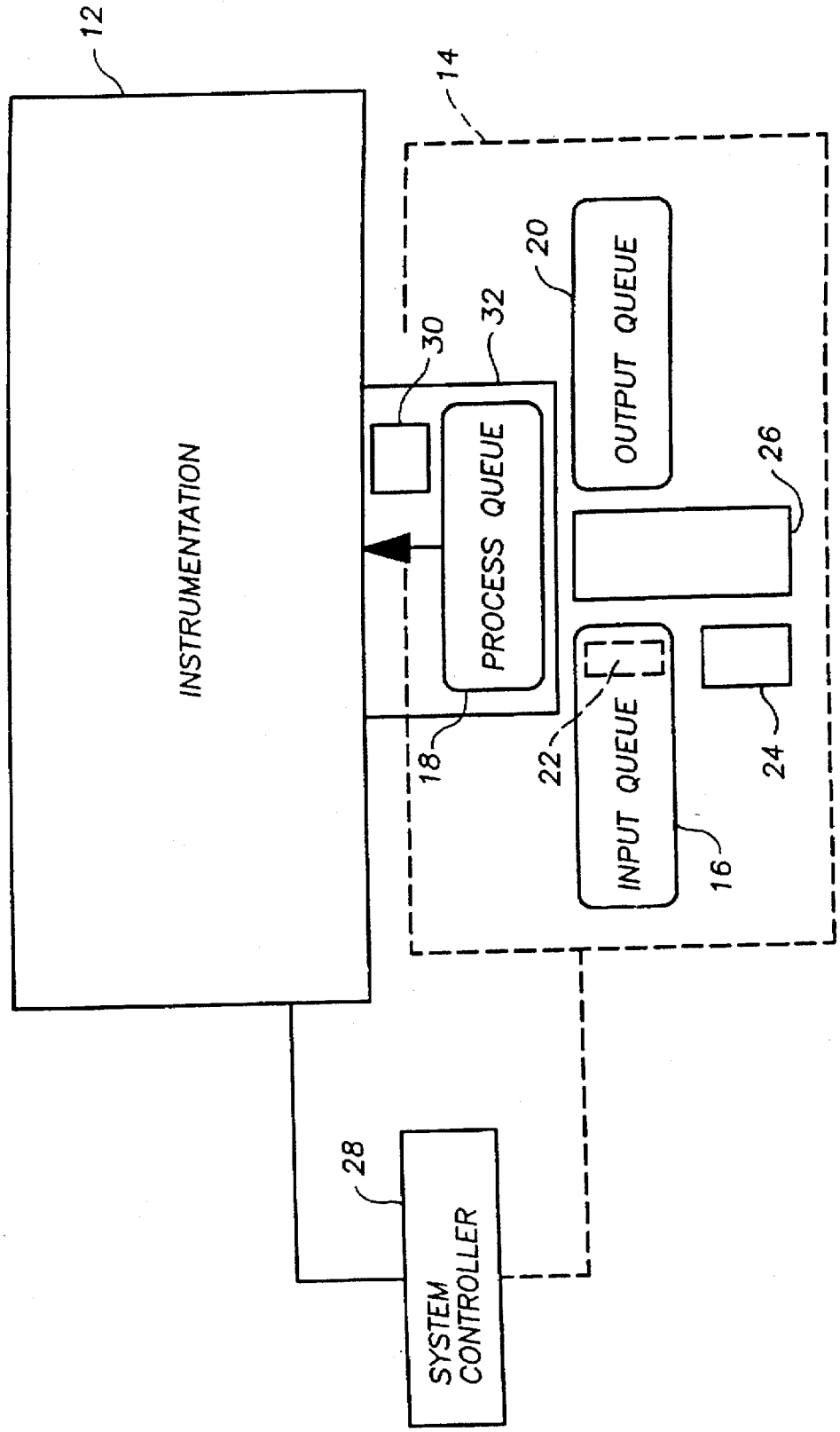
FIG. 1 is a block diagram of an automated analyzer instrument.

Referring now to FIG. 1, an automated analyzer instrument 10 used to perform diagnostic tests on test samples includes instrumentation generally denoted 12 and a transport system 14. The instrumentation 12 may typically include an incubation chamber and processing stations similar to the types described in co-pending patent application Ser. No. 08/338,022 filed on Nov. 10, 1994 and assigned to the assignee of the present invention, a luminometer which may be similar to the type described in co-pending patent application Ser. No. 08/035,341 filed on Mar. 19, 1993 and Ser. No. 08/366,003 filed Dec. 20, 1994 both also assigned to the assignee of the present invention and a fluid moving system generally provide from pipettes controlled by robotic arms. Each of the above identified applications are incorporated herein by reference. The transport system 14 allows a continuous supply of samples for uninterrupted testing.

The transportation system 14 includes an input queue 16, a process queue 18 and an output queue 20. The input queue 16 moves sample-containing vessels such as test tubes, for example, toward a load position 22 located at one end of the input queue 16. The test tubes hold samples of patient bodily fluid specimens and the like to be analyzed by the analyzer instrument 10. Once the test tubes reach the load position 22, an infeed apparatus 24 moves the sample-containing test tube from the input queue 16 to a predetermined position on the process queue 18.

As the test tubes move from the input queue 16 to the process queue 18, the test tubes pass by a bar code reader 26 disposed proximate the load position 22 of the input queue 16. The bar code reader 26 deciphers a bar code typically attached to each test tube and to each rack by a label and transmits its information to a system controller 28 which performs a variety of functions including tracking the samples provided to the process queue 12 and scheduling the order in which the samples are tested.

Once a test tube is moved in a sample rack to the process queue 18 the instrumentation apparatus 32 aspirates a portion of the sample from the test tube and subsequently dispenses the sample portion into a reaction container such as a cuvette positioned in the instrumentation apparatus 11, where it is treated according to the above identified application '022.

After the sample is aspirated from the test tube and dispensed into the reaction container, the sample rack is generally held in the process queue until the test result is obtained. Thus, if a bad test result occurs the test can be rerun by aspirating a second portion of the sample from the test tube and dispensing the second portion into another reaction container. Once each sample in a sample rack has been successfully tested, the process queue 18 positions the sample rack in front of an exit apparatus 30 which moves the sample rack from the process queue 18 to the exit queue 20. Once the test tube is moved to the exit queue 20, the sample-containing test tubes are again accessible to a user and are typically removed from the transport system 14 periodically.

The process queue 18 is enclosed in protective housing 32 to prevent a user from accessing sample-containing test tubes after the test tubes have been moved from the input queue 16 to the process queue 18. Thus while the test tubes can be easily accessed and randomly ordered and arranged and re-arranged while on the input queue 16, the placement and ordering of the samples cannot be changed by a user once the samples are moved to the process queue 18 where controller has a record of their position.

Referring now to FIG. 2, 3, 3A and 4 a transport system 14 includes an input queue 16, a process queue 18 and an exit queue 20. A plurality of sample racks generally denoted 33 are disposed on the input queue 16 which is provided having a generally rectangular shape. Each of the sample racks 33 is adapted to hold a plurality of sample-containing test tubes generally denoted 34 and thus the sample racks 33 allow multiple test tubes 34 to be simultaneously moved from the input queue 16 to the process queue 18 and from the process queue 18 to the output queue 20.

In operation, one or more sample racks 33 may be placed by a user in any location on the input queue 16. While sample racks 33 are being moved along the input queue 16, the user can remove or arrange the sample racks 33 in a random or a predetermined order. Thus, the input queue 16 is typically an area of the automated analyzer instrument 10 (FIG. 1) which is highly accessible to a user.

The input queue 16 is provided from a tray 38 having a rectangular shape and having a width W corresponding to an exemplary distance typically of about 5.2 inches and an exemplary length L corresponding to a distance typically of about 17.5 inches. The width W of the tray 38 should be selected to accommodate the length of the sample racks 33 and the length of the tray L should be selected to accommodate a number of sample racks 33.

The sample racks 33 are loaded onto a first surface of the tray 38a such that a handle 39 of each of the sample racks 33 is positioned at a side of the tray 38 proximate the user. The handle 39 allows a user to easily hold and thus move and arrange sample racks 33 on the tray 38.

Each of the sample racks 33 has a top surface 33a with a plurality of openings therein in which test tubes 34 may be disposed, a front-end, a back-end and a bottom surface having recesses 40 formed therein.

The tray 38 includes a raised central portion 42 extending its length. The raised central portion 42 serves as a guide along which the sample-rack 33 travels as the sample rack 33 moves from a first end to a second end of the input tray 38 (left to right in the figure).

The guide 42 may be provided as a piece separate from the tray 38, or preferably, the guide 42 may be provided as an integral part of the tray 38 as by plastic injection molding or stamping in aluminum. The guide 42 should be provided having a height selected to insure that the sample rack 33 does not catch on or become entangled on the guide 42.

The tray 38 further includes a back edge guide 44 which engages a slot 46 in the back-end of the sample rack 33 to prevent the sample rack 33 from becoming dislodged from the tray 38 and to prevent the rack from tipping.

The tray 38 is disposed on a housing 50 which encloses a drive system for the rack 33. The drive system moves the sample racks 33 along the top surface of the input tray 38 via a magnetic force generated on the underside of the tray 38. The tray 38 and housing 50 cover the drive system and thus isolate the drive system from the user environment.

Since the tray 38 and the housing 50 completely enclose the drive system safety hazards due to exposure of a user to moving parts of the drive system are minimized. Furthermore, the tray 38 and cover 50 prevent fluid spills and other undesirable elements (e.g. dust and dirt) from contaminating the drive system or other areas of an analyzer system to which the transport system 14 is coupled and with which the sample transport system 14 cooperates. Also, since the user is not exposed to any moving parts, the drive system need not be shut down prior to or during cleaning of the tray 38 in order to prevent injury to a user or interference by a user with the operation of the drive system.

Moreover, since the surface of the tray 38 is without openings, the tray 38 is relatively easy to clean. Cleaning of the tray 38 is further unimpeded by sample rack positioning structures. This also allows the sample racks 33 to be arbitrarily loaded onto, removed from or rearranged on the tray 38 without interruption of the operation of the transport system 14.

The process queue 18 is disposed adjacent the input queue 16 such that sample racks 33 may be conveniently and easily moved from the end of the input queue 16 to the process queue 18. In this embodiment, the process queue 18 is mounted on a movable carrier member 52.

Disposed on the carrier member 52 is a support block 54 which may be provided, as an aluminum member having a square cross-sectional shape and having a thickness typically of about one inch. The support block 54 supports a slide 58 a predetermined distance above the carrier member 52, and provides additional structural support to the carrier member 52. A drive 53 is coupled to move the process queue 18 in response to signals from controller 28.

A process tray 60 mounts on the slide 58 to move on linear bearings mounted on a bottom surface of the process tray 60.

The process tray 60 is provided having a plurality of equally spaced dividing walls 61 projecting from a base surface thereof. The dividing walls 61 form a plurality of slots 64 in which sample racks 33 may be held.

An infeed apparatus 51 is mounted at a predetermined position on the input queue 16. In the embodiment shown the infeed apparatus 51 is mounted at an end of the tray 38. The infeed apparatus 51, which will be described in detail below in conjunction with FIGS. 3 and 4, moves the sample rack from the load position at the far end of the input queue 16 to an empty slot 64 of the process queue 18. The process tray 60 is directed by controller 28 to a position to insure that an empty slot 64 is available to receive the sample rack 33 provided by the infeed apparatus 51.

The process tray 60 typically has mounted on one end or the other a probe tip tray 62 in a carrier 68. The probe tip tray 62 has a plurality of holes 66 in which a plurality of disposable probe tips 70 are arranged.

The transport system 14 further includes an exit pusher 72 having a push rod 74 driven by a motor drive 76. The motor drive 76 drives the push rod 74 through a slot 64 whereby a sample rack 33 is moved from the process queue 18 onto a surface 78a of an exit tray 78 of the exit queue 20 under control of controller 28.

The exit tray 78 includes a guide 80 similar to the guide 42 on the input tray 38. Guides 42, 44 80 and 99 are absent where the sample racks are moved to and from the process queue. Once a sample rack 33 is moved from the process queue 18 to the exit queue 20, an index mechanism, which will be described in detail in conjunction with FIG. 3A below, moves the sample rack along the top surface of the exit tray 78.

In this particular embodiment, the input queue 16 is selected having a tray long enough to hold twenty sample racks 33. In this particular embodiment, each sample rack 33 holds five test tubes 34.

Each of the test tubes 34 have a bar code label attached thereto. The test tubes 34 are oriented in the sample rack 33 such that the affixed bar code label is exposed to a bar code reader 83 disposed proximate a load position 22 of the input queue 16, where sample racks are moved out of the process queue.

The infeed mechanism 51 is here shown to include a belt 84 endlessly circulating around a pair of pulleys 86a, 86b. As may be more clearly seen in FIG. 4, a first one of the pulleys 86a is coupled to a bidirectional motor 104 such as a stepper motor.

Referring again to FIG. 3, coupled to the belt 84 are a plurality of outwardly extending paddles or profiles 88, 88a–88b. The profiles 88 are placed on a portion only of the belt 84. The locations of the end profiles 88a, 88h are selected such that a sample rack 33 can be positioned in the load position 22 between them while the profiles 88b–88h prevent a sample rack 33a adjacent the load position 22 from entering the load position as a rack is moved off between profiles 88a and 88h.

In one embodiment, the belt 84 and, profiles 88 are urethane and may be manufactured as integral pieces using injection molding techniques. Alternatively, the profiles 88 may be manufactured as pieces separate from the belt 84. In this case the profiles can be attached to the belt 84 via ultrasonic welding or any other fastening techniques well known to those of ordinary skill in the art.

Coupled to the input queue 16 proximate the load position 22 is a load position guide 89. The load position guide 89 prevents tipping of the sample rack in the load position 22.

When the belt 84 turns in a counterclockwise direction thus moving the profiles 88 to a position opposite the sample racks 33 disposed on the input tray 38, the load position is available to accept a sample rack 33. The sample rack 33 which was adjacent the profiles 88 is then moved into the space of load position 22 where its presence is sensed by a sensor as described below.

The motor 104 (FIG. 4) then drives the belt 84 and profiles 88 in a clockwise direction. Coupled to profile 88a is an aluminum block 90 which contacts a first end of the sample rack 33 which is now placed in the load position 22 of the input queue 16. As the belt 84 moves in a clockwise direction, the sample rack 33a is pushed from the load position 22 of the input tray 38 to an open slot 64 in the process queue 18 by controller 28.

Block 90 extends the distance which the surface contacting the end of the sample rack 33 travels ensuring that the sample rack 33 is pushed completely off the input queue 16 and completely on to the process queue 18.

The process queue 18 accepts the sample racks 33 fed thereto by the infeed mechanism 51. As described above, the process queue 18 moves linearly along a track such that sample racks 33 from the input queue 16 may be fed into different spaces 64 of the process queue 18. Also the process queue 18 moves along the track to align particular sample racks 33 with the exit pusher 72 under control of controller 28.

The process queue 18 positions sample racks 33 whose samples have been successfully tested in the process queue 18 in front of the exit pusher 72. The exit pusher 72 includes the push rod 74 driven by a bidirectional motor 76. At position 97, a pusher 108 (FIG. 3A) in a pusher assembly 100 pushes the sample rack out onto the exit queue.

A sensor 98 at an end of the exit queue 20 indicates to the controller 28 when the exit queue 20 fills with sample racks 33 a signal and either notify a user to take some action such as removing sample racks 33 from the exit queue 20 and/or prevent any additional sample racks 33 from being moved from the process queue 18 to the exit queue 20 until space is made available on the exit queue 20. The sensor may be disposed on a top or bottom surface of the tray 78.

The transport system 14 also has an emergency sample rack entry queue 105. Entry queue 105 includes a stat-entry position 101, a star sensor 102 and a star-load position 103. The purpose of the stat-entry queue 105 is to allow a user to have the analyzer system 10 perform a test out of order as soon as possible on any samples loaded the in stat-entry queue 105.

When a user places a sample rack 33 into the stat-entry position 101, the stat sensor 102 activates pusher block 108 (FIG. 3A) which pushes the sample rack from the stat-entry position 101 to the star-load position 103 with profiles 88 set to the appropriate side of belt 84. A star-load position guide 113 is disposed proximate the stat-load position 103 to prevent tipping of the sample rack in the stat-load position 103. The infeed apparatus 51 then moves the sample rack from the star-load position 103 to process queue 18 by reverse rotation of the belt 84.

The transport system 14 further includes the bar code reader 83 disposed proximate the stat-entry position 101.

Portions of the bar code reader 83 have here been removed to allow a clearer view of the pusher bar 106 and pusher block 108. The bar code reader 83 is held in a fixed position above the pusher block 108 by a mounting member 109 which may be provided as a mounting bracket for example. The bar code reader 83 is preferably positioned such that it can read bar codes on labels attached to the test tubes being moved to the process queue 18 from either the load position 22 (FIG. 3) on input queue 16 or from the stat-load position 103.

As the sample racks 33 and thus test tubes are moved from the input tray 38 to the process queue 18, the bar code labels move past the bar code reader 83 and the bar code reader 83 decodes the information from the bar code label and sends such information to the system controller 28 (FIG. 1). This information may include, patient, sample, and other direct fluid data. Tests to be run on each sample are entered separately into controller 28. Some samples may be identified for "batch runs" meaning a specified set of tests for all specimens in the batch.

Referring now to FIGS. 5, 5A, 5B, 6, 7 and 8, a magnetic conveyor 110 is provided for the input queue 18. Below the transport tray 38 is a drive system 116. In this particular embodiment, the drive system 116 includes first and second drive belts 117 disposed around a pair of pulleys 118a, 118b, driven by a drive motor 119. Belts 117 are placed near front and back portions of tray 38.

Figure 5:
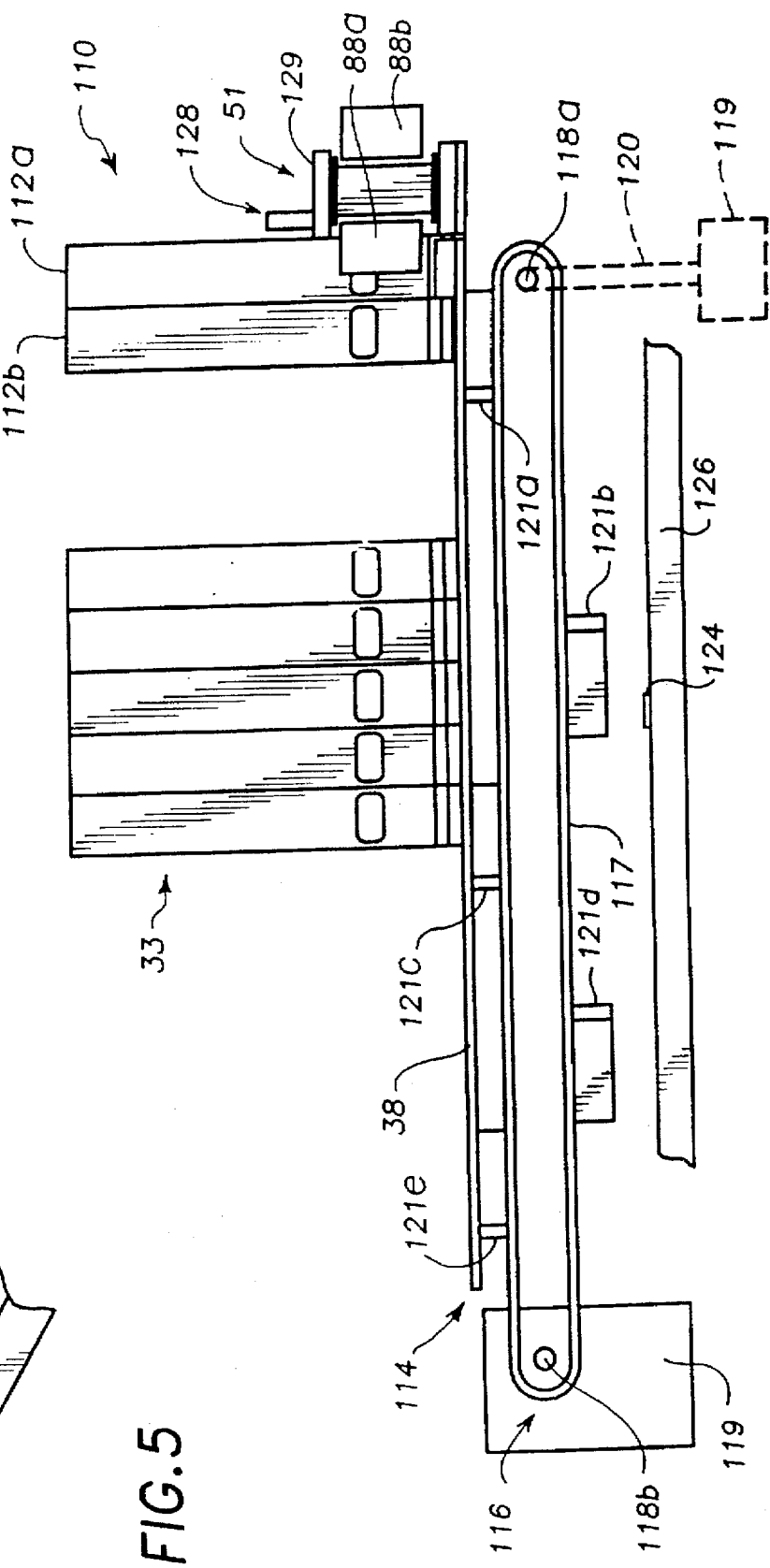
FIG. 5 is a portion of a side view of a sample transport system.

Referring briefly to FIGS. 5, 5A and 5B the drive motor 119 is here provided as a stepper motor 119 having a drive gear 123 coupled to pulley 118b which is provided as a pulley gear 118b (FIG. 5B). The coupling is accomplished with a 2:1 gear reduction ratio.

In an alternate embodiment of the drive system 116, here shown in phantom, the drive motor 119 may be disposed below the transport tray 38 and coupled to pulley 118a via a drive belt 120.

A plurality of magnet assemblies 121a–121e are coupled to each drive belt 117. The magnet assemblies 121a–121e are equally spaced apart by a predetermined distance. The tray 38 is spaced a predetermined distance above the belt 117 such that the magnet assemblies 121a, 121c and 121e as shown in FIG. 5, pass under the tray 38 a predetermined distance. Each magnet assembly 121a–121e includes a magnet having a magnetic force of sufficient strength such that a magnetic force is present at least at, and in this embodiment preferably above, the surface 114a of the tray 78.

The sample racks 33 include a magnetically attractive region engageable by the magnetic force of magnet assemblies 121. The magnet assemblies 121 thus magnetically couple the sample racks 33 to the drive system such that drive system moves the sample racks 112 along the surface of the tray 38.

In the present embodiment, five magnet assemblies 121a–121e are driven around the pair of pulleys 118 via the belt 117 and move the sample racks 112 along the transport tray 114. The distance by which the magnet assemblies 121 are spaced from each other is selected in accordance with a variety of factors including but not limited to the number of sample racks 33 each individual magnet assembly 121 can move. In this particular embodiment, each magnet assembly 121 is of a magnetic strength sufficient to move several sample racks 33. Those of ordinary skill in the art will recognize of course that more or fewer magnet assemblies 121 could alternatively be used. The conveyor system 110 further includes a sensor 124 coupled to a base plate 126 and disposed below a surface of the belt 117. The sensor 124 may be provided as a Hall effect sensor, for example, and is disposed to provide a signal whenever a magnet assembly 121 passes thereover. The sensor 124 thus indicates the position of a magnet assembly 121. Since the location of each of the magnet assemblies 121a–121e on the belt 117 with respect to the other is known, when the location of one of the magnet assemblies 121 is known, the location of each of the magnet assemblies 121 is known.

Figure 10:
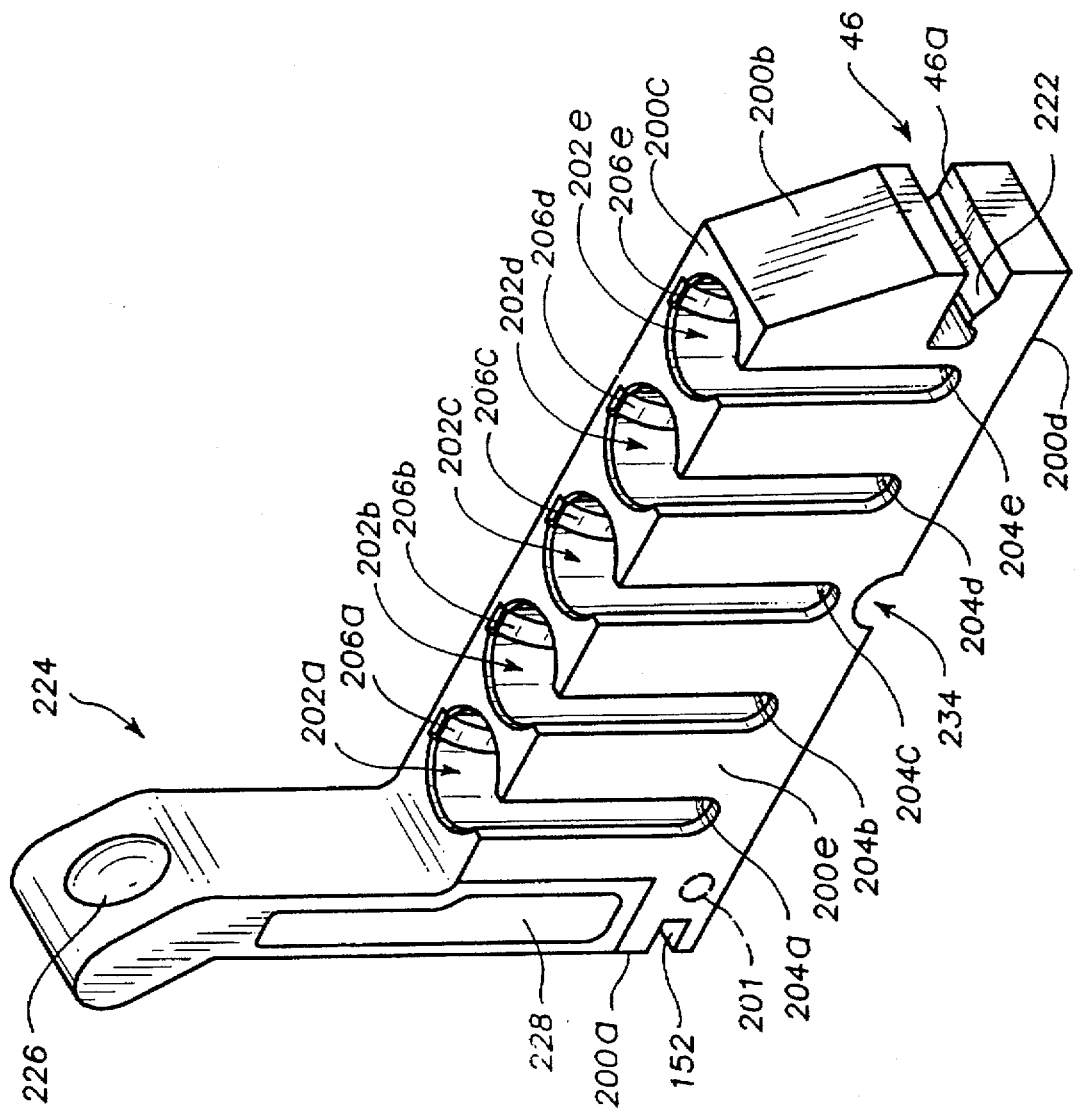
FIGS. 10 and 11 are a series of perspective views of a sample rack.

The transport system 110 further includes a load position sensor 128 which may, for example, be provided as an optical sensor which detects light reflected from a surface of a sample rack 33 adjacent it. In operation, as a sample rack 33 moves into the load position in front of profile 88a, light reflects off a surface 201 (FIG. 10) of the sample rack 33 and activates the load position sensor 128.

In response to a signal provided by the load position sensor 128, the drive motor 119 coupled to pulley 129 turns the belt 117 in a clockwise direction until, typically three magnet assemblies 121 pass by the sensor 124. This step ensures that any sample rack 33 positioned on the left most side of the tray 38 travels the entire length of the tray 114.

Figure 3:
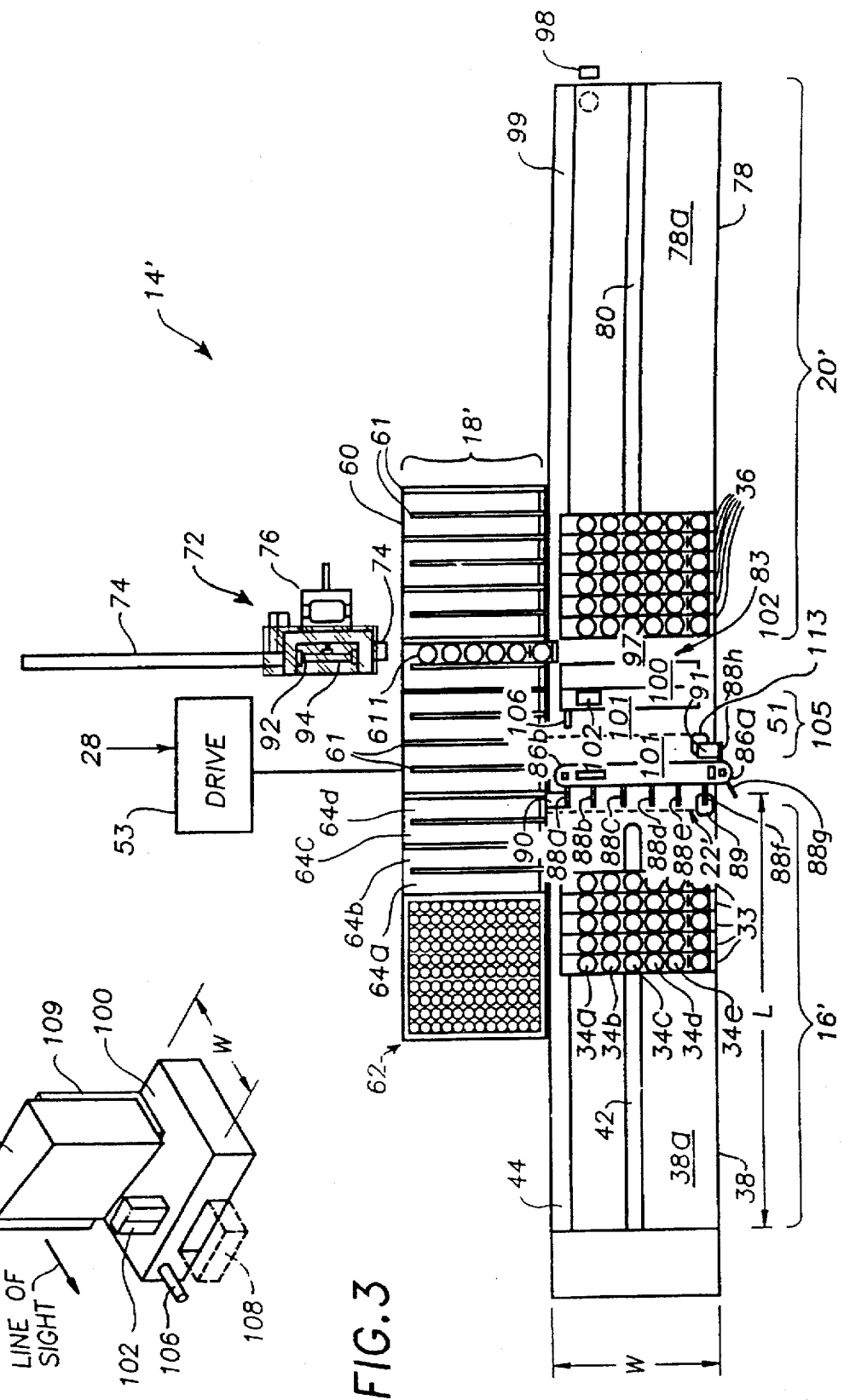
FIGS. 3 and 3A are a top view of a sample transport system.
Figure 3A:
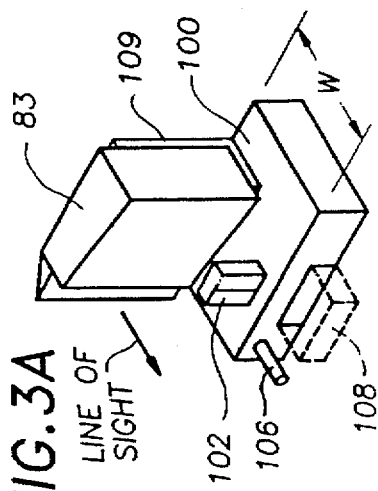
Figure 4:
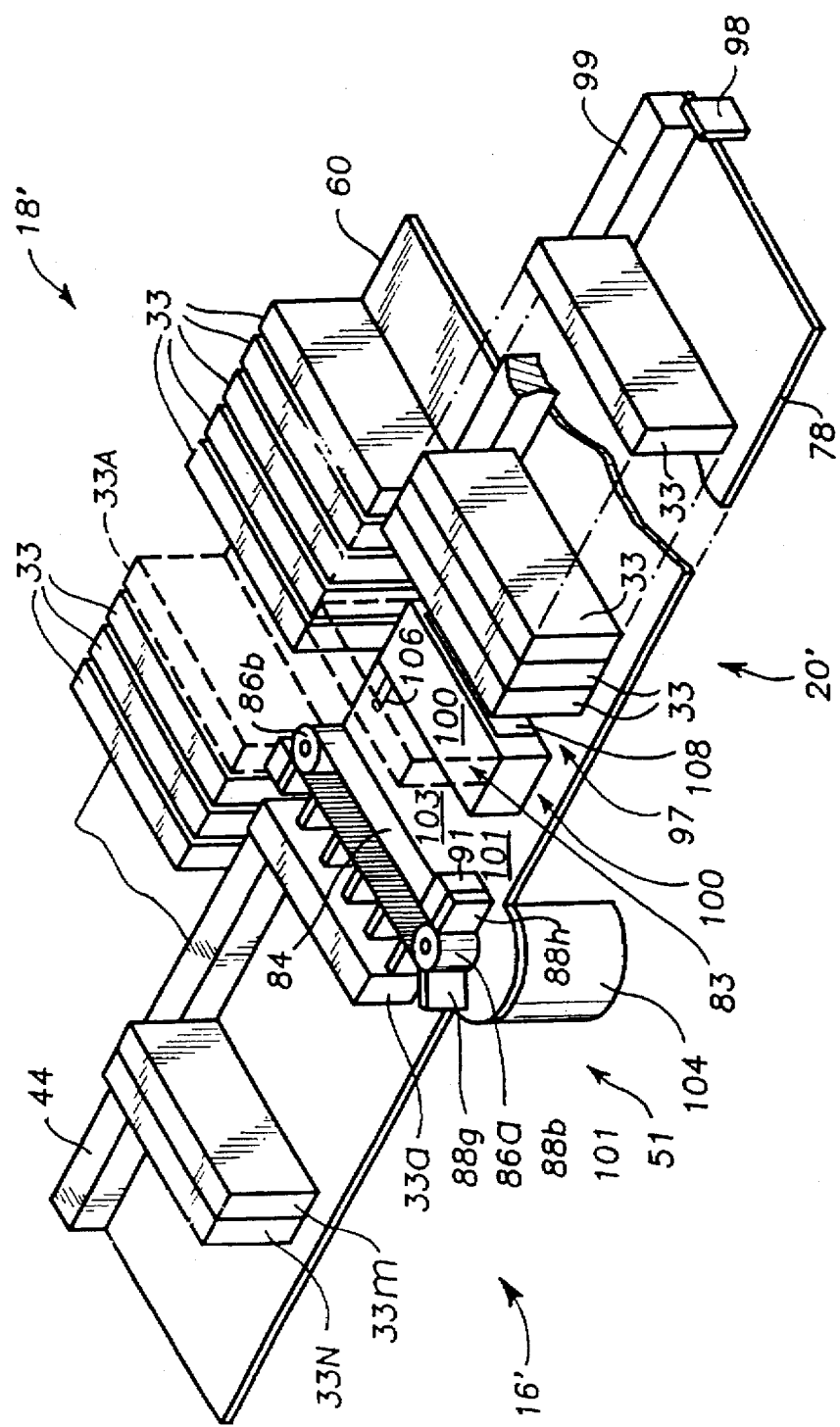
FIG. 4 is a perspective view of a sample transport system.

The drive motor 119 then turns the belt 117 in a counterclockwise direction by a predetermined short distance typically 0.06 in.) to relieve any pressure applied to a sample rack in the load position due to an adjacent sample rack. By reducing forces on the sample rack in the load position, the infeed apparatus 51 can more easily drive the sample rack from the input queue 16 (FIG. 3) to the process queue 18 (FIG. 3).

It should be noted that the drive system, here provided from the belt 117, pulleys 118 and motor 119 is completely independent of the tray 38 and magnet assemblies 121. Thus the drive system 116 may be alternatively implemented by any means for moving the magnet assemblies 121 such as electromagnetic means or other means.

For example, the magnet assemblies may be provided as having electromagnets which may be turned on and off to attract the magnetically attractive regions of the sample racks. Such electromagnets may be moved via a conveyor type belt similar to belt 117 or via pusher rods which move back and forth in a linear direction below the tray. With the pusher rod approach the electromagnets would be activated as the push rods move the magnets and thus sample racks from a position distal to the load position to a position proximate the load position. The electromagnets would then be de-activated prior to the push rods retracting the electromagnets from the load position. Furthermore, with the input tray completely filled, in the case where electromagnets are used on belt 117, it need not be turned off to prevent magnet forces from continuously pushing against the sample racks, rather, the electromagnets may be turned off.

Figure 6:
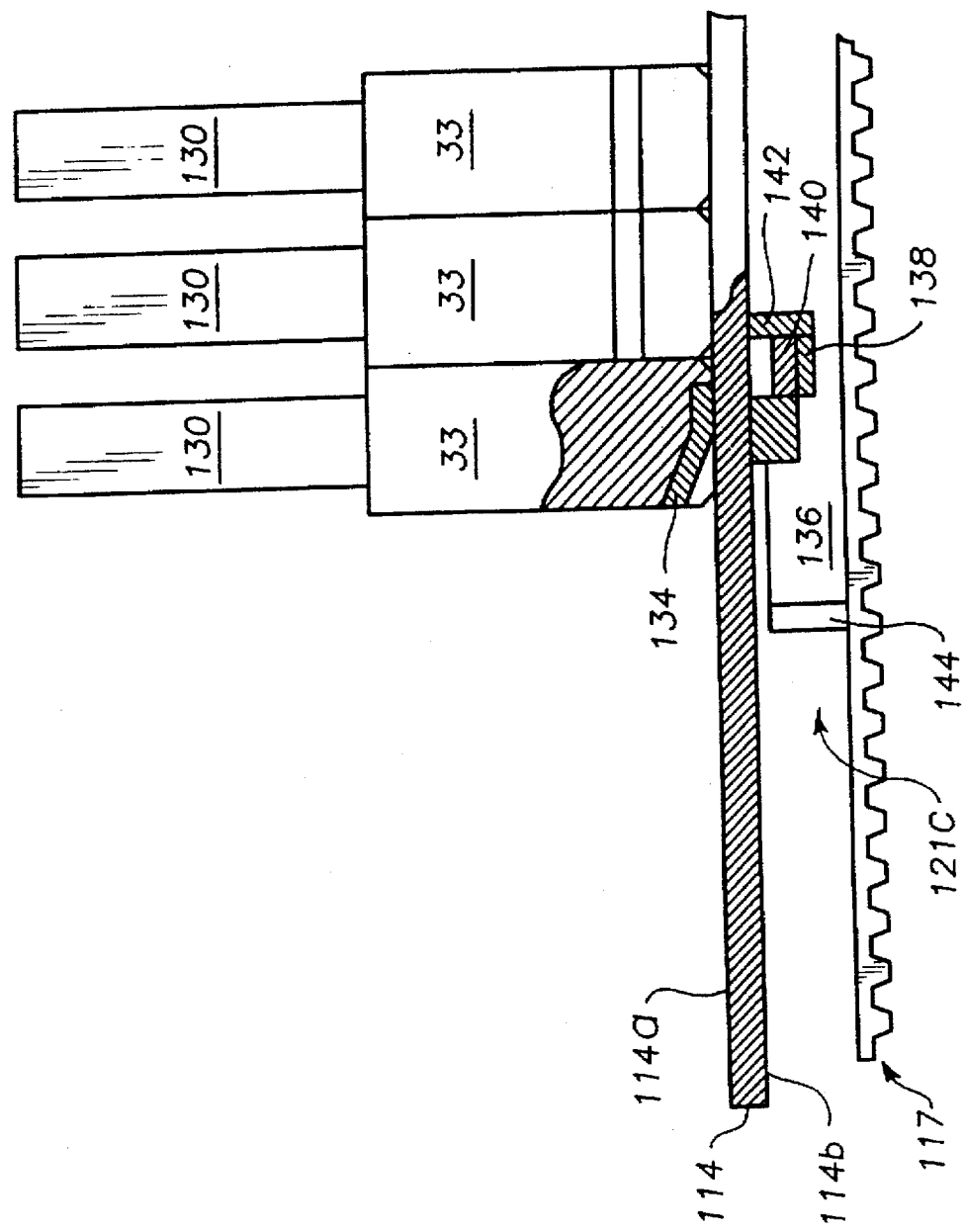
FIG. 6 is a cross sectional view of a sample rack and a magnet assembly.

Referring now to FIG. 6, a portion of the magnetic conveyor 110 described above in conjunction with FIG. 5, is shown having three sample racks 33 disposed thereon. Top portions of each of the sample racks 33 have been removed to reveal test tubes 130 disposed in each of the sample racks. A bottom portion of the sample rack 33, has been cut away to expose in section, a plate 134 disposed in a bottom portion of the sample rack 33. The plate 134 may be provided from any magnetically attractive material.

In this particular embodiment, the plate 134 is provided from magnetic stainless steel having a thickness typically of about 0.125 inches. In alternate embodiments, however, other materials such as iron, non-stainless steel or even a magnet material may also be used. In the event that plate 134 is provided from a magnet material care should be taken to ensure that a magnetic pole of plate 134 is not in opposition to a magnetic pole of magnet assembly 121.

The magnet assemblies 121 include an aluminum housing 136 having a thickness typically of about 0.090 inches over which shown in section, a backing plate 138, a bar magnet 140 and a magnet cover 142, are disposed. The backing plate 138 is provided from magnetic stainless steel and is provided having a thickness typically of about 0.060 inches. The magnet 140 may be provided as a neodymium-iron-boron magnet having a thickness typically of about 0.250 inches and the magnet cover 142 may be provided from a plastic material such as Acetal or any similar material having a thickness typically of about 0.040 inches.

The magnet assembly 121 is coupled to a profile 144 projecting from a surface of the belt 117. The profile 144 may be similar to the profiles 88 described above in conjunction with FIGS. 3 and 4.

The magnet assemblies 121 can be coupled to the profile 144 via screws which pass through clearance holes provided in the profile 144 and mate with threaded holes provided in the aluminum housing 136 or may be fastened to the profile 144 via epoxy or welding techniques well known to those of ordinary skill in the art.

The backing plate 138 is provided to increase the strength of the magnetic field provided by the magnet 140 by providing a return path coupling assemblies 121 for each belt 117. The backing plate 138 also modifies the configuration of the magnetic field provided by magnet 140. The magnet 140 is spaced a distance below the tray surface such that the magnetic field is concentrated in a region at or above the surface of tray 38 upon which the sample racks 33 are disposed. A first edge of the plate 134 forms a right angle with the tray surface thus generating a relatively strong magnetic couple such that the magnet assemblies 121 can pull the sample racks 33. A second, rearward edge of the plate 134 is provided having an angled surface as will be described further below.

The tray 38 is, in this embodiment, provided from an aluminum sheet having a thickness typically of about 0.0625 inches. The surface of the aluminum sheet on which the sample racks 33 are disposed is provided having a polytetrafluoroethylene type of coating, such as Teflon® disposed thereon to reduce frictional forces between the tray 38 surface and the contacting surface of the sample racks 33. It should be noted that the belt 117 is spaced a distance below the tray surface 38 such that a top surface of the cover 142 contacts or is slightly spaced below the tray surface 38.

Figure 7:
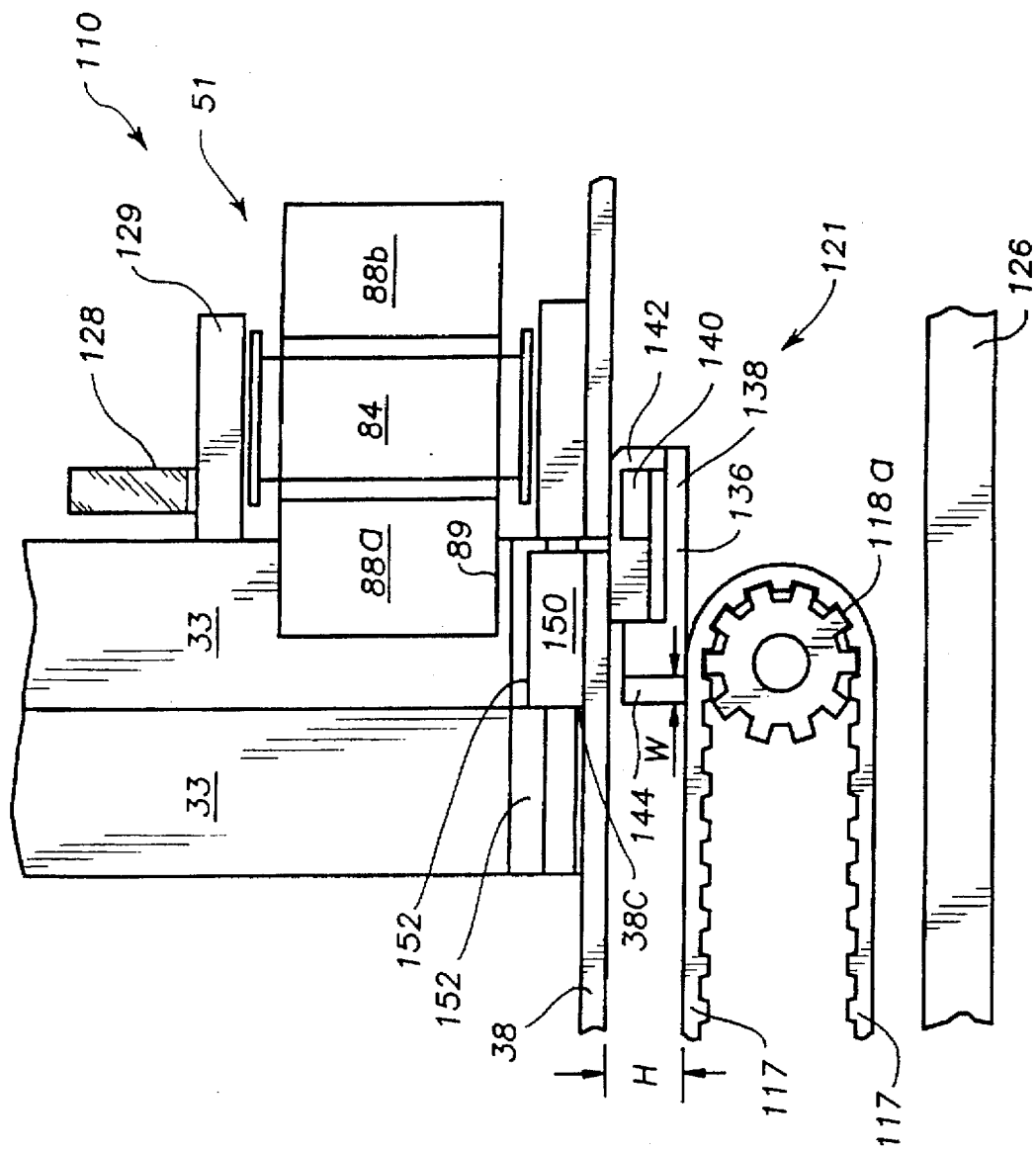
FIG. 7 is a side view of a portion of a sample transport system.

Referring now to FIG. 7, a portion of the conveyor system 110 is shown having sample rack 33 disposed in the load position of an input queue. As can be seen in FIG. 7 the load position corresponds to a channel defined on one side by a shoulder 38c of the tray 38. A load position guide 150 is disposed proximate the load position. In operation, as the sample rack 33 is moved into the load position of the input queue, the load position guide 150 engages a slot 152 formed in the front end of the sample rack 33. The guide 150 ensures that the sample rack 112 is properly aligned in the load position.

When the sample rack 33 reaches the load position, the sensor 128 sends a signal which under control of controller 38 activates the infeed apparatus 51 and causes the belt 84 to turn the profile 88a and member 90 (FIG. 3) to drive the sample rack 33 onto the process queue. Taking profile 88a as representative of profiles 88, the profile 88a is provided having a height H typically of about one inch, a width W typically of about 0.750 inches and a thickness T typically of about 0.125 inches. A bottom edge 89 of profile 88a is spaced a predetermined distance from the top surface of the tray 38, typically of about 0.25 inches.

As described above, the magnet assembly 121 is coupled to the profile 144 projecting from the belt 117. As the magnet assembly 121 approaches the end of the tray 38 proximate the profiles 88 and pulley 118a, the magnet assembly 121 is extended past the end of the pulley 118a, insuring that the sample rack 33 is moved completely into the load position of the tray 38. Thus, by coupling the magnet 140 to the profile 144 as described above, the magnet assembly 121 moves the sample rack 33 past the end of the belt 117 as it rounds the pulley 118a.

As can be clearly seen in FIG. 7, the pulleys 118a or 118b have sets of teeth to engage corresponding recesses in the belt 117 to preserve indexing.

As mentioned above in conjunction with FIG. 6, once the sample rack 33 is placed in the load position, the pulleys 118 turn to move the belt 117 an additional distance to move any other sample racks 33 on the tray 114 toward the load position. The belt 117 stops moving, with one of magnet assemblies 121 positioned by controller 28 under the sample rack which is next in line to be moved to the load position when the belt 112 executes a short move back away from the load position, the sample rack 37 in the load position remains in the load position while the other sample racks 33 moves away slightly to prevent jamming at the load position.

Figure 8:
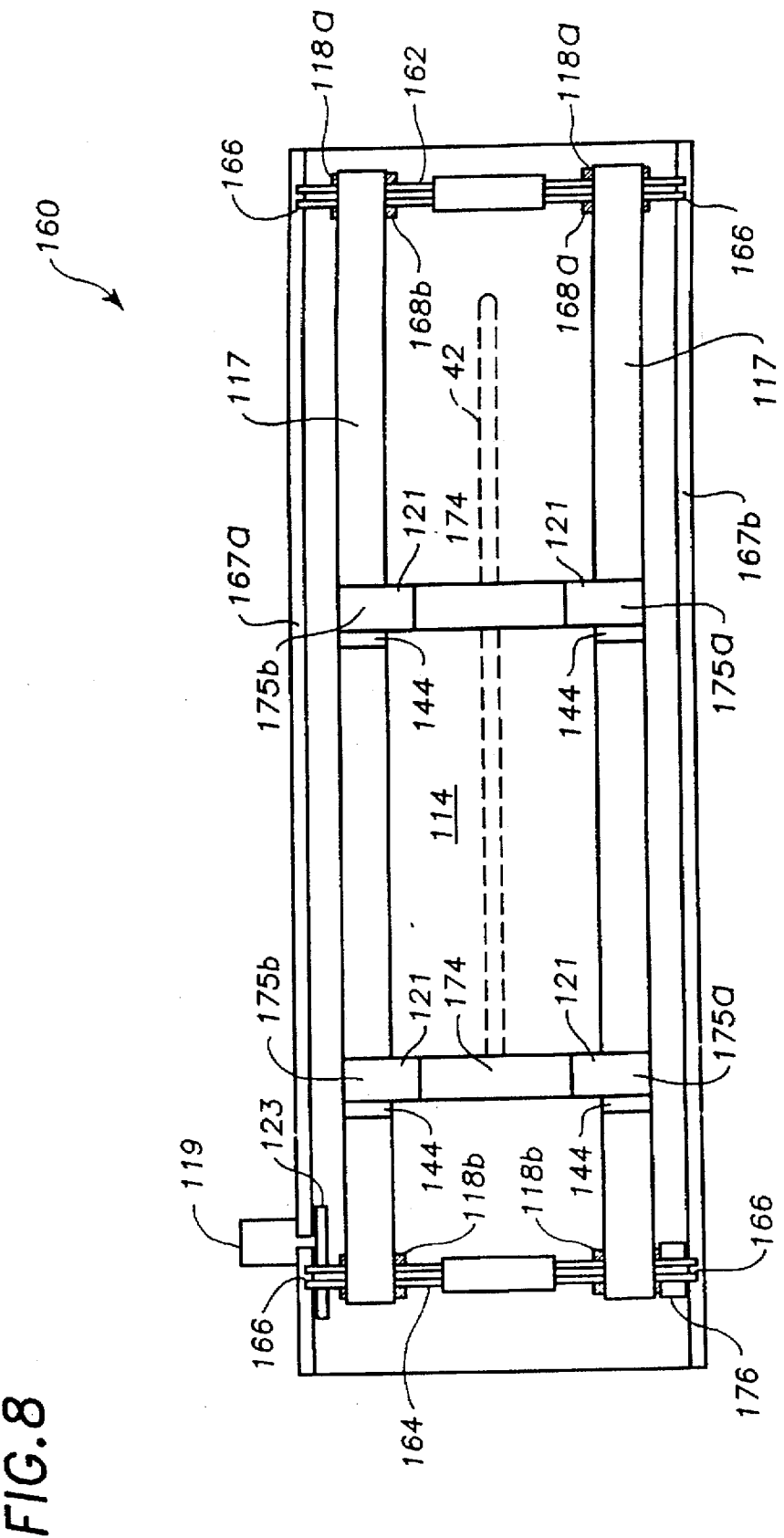
FIG. 8 is a bottom view of a drive system.
Figure 9:
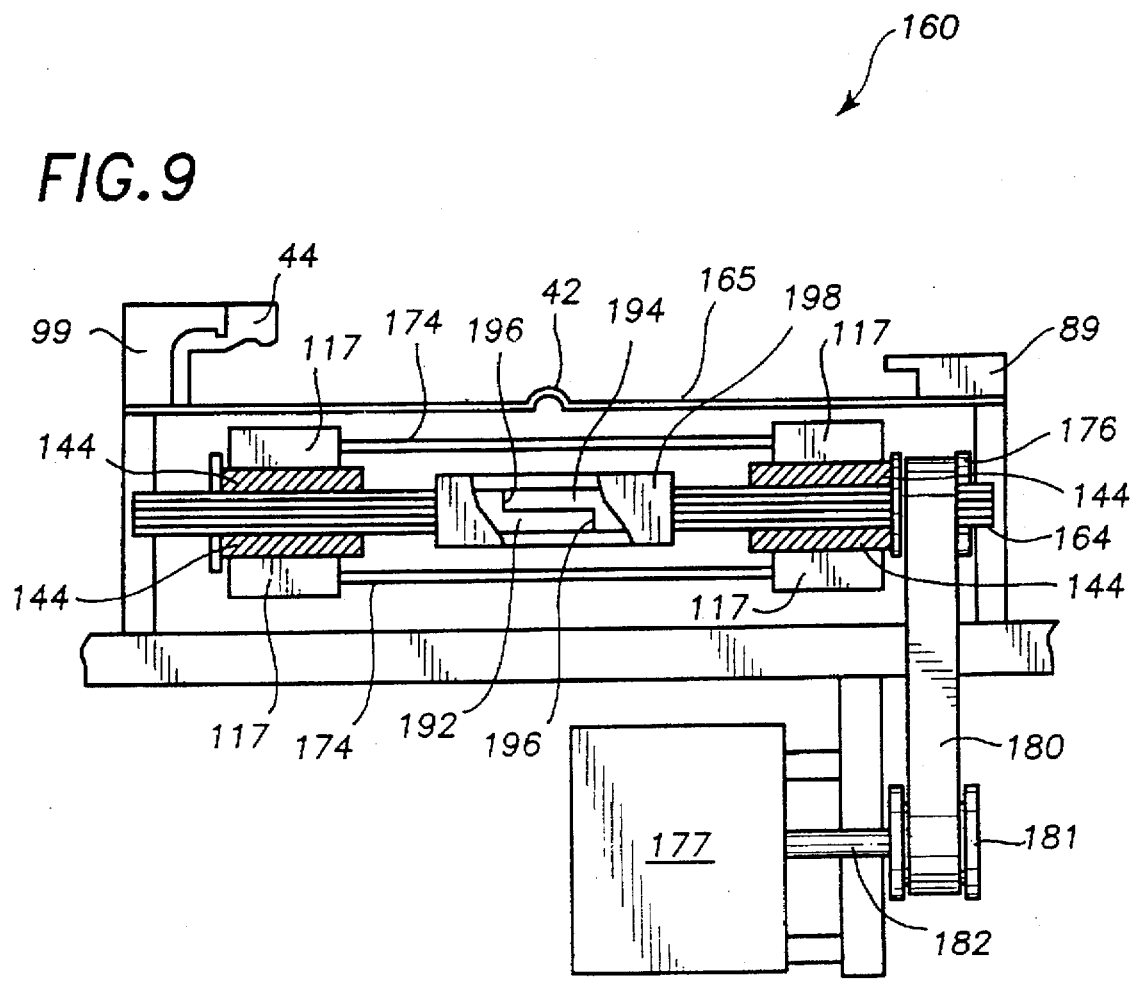
FIG. 9 is an end view of an alternative drive system.

Referring now to FIGS. 8 and 9, in a bottom view the drive assembly 116 is shown to include a pair of like stainless steel shafts 162, 164 spaced apart and disposed at opposing ends of tray 114. Taking shaft 164 as representative, each end of the shaft 164 is coupled to a ball bearing assembly 166 mounted as shown in respective ends of mounting plates 167a, 167b generally denoted 167 extending below tray 114. The ball bearing assemblies 166 allow the shafts 162, 164 to rotate relative to the mounting plates 167. Each shaft 162, 164 has mounted thereon the paired drive pulleys 118a, 118b. Disposed adjacent one belt pulley 118b is a drive gear 123. In FIG. 9 an alternate drive pulley 176, is coupled to a shaft 164, and driven by a drive motor 177 the through shaft 122, pulley 181 and belt 180.

As may also be clearly seen in FIG. 9, the drive shaft 162 is here provided from a pair of shafts 192, 194 held together by a combination of shoulder regions 196 and a locking collar 198. By providing the shafts 162, 164 from a number of separate pieces, the shafts 162, 164 can be easily assembled and disassembled to allow easy access for repair and replacement.

As can also be seen clearly in FIG. 9 an input queue back edge guide 44, a load guide 89, and an output queue back edge guide 99 are disposed on the tray 114.

Referring now to FIGS. 10–17, a sample rack 200 corresponding to rack 33, has first and second opposing ends 200a, 200b, a top surface 200c, a bottom surface 200d (FIG. 14) and a pair of opposing side surfaces 200e, 200f (FIG. 16). An optional reflective member 201 is disposed on surface 200e. The reflective member, 201 reflects light to activate optical sensor 128 (FIG. 5). Thus, the reflective member can be disposed along any portion of surface 200e where it may be aligned to activate sensor 128. Alternatively and preferably, member 201 is omitted (FIG. 11) and surface 200e is made of a reflective material or polished such that light incident thereon is reflected and activates sensor 128.

A plurality of openings 202a–202e are formed in top surface 200c of rack 200 in the typical case there are five openings. The openings 202a–202e are provided having a shape selected to accept a sample containing vessel. In this particular embodiment, the openings 202 are provided having a circular shape selected to accommodate test tubes in a range of sizes. Each of the openings 202a–202e has a corresponding slot 204a–204e formed in the side surface 200e of the sample rack 200.

The slots 204a–204e extend from the top of the respective openings 200a–200e toward the bottom surface 200d of the sample rack 200. Disposed in each of the openings 202a–202e is a finger spring 206a–206e. Here openings 202 are provided having a length typically of about 1.7 inches and a diameter typically of about 0.675 inches. Springs 206 are provided having a length typically of about 1.5 inches and a width typically of about 0.313 inches and slots are provided having a width typically of about 0.345 inches. The slot walls 205 (FIG. 11) are provided having a thickness typically of about 0.08 inches and along with spring 206 provide a three point contact (2 lines and a point between the edges of slots 204 and the center part of springs 206) to thus secure test tubes of various sizes in the openings 202 of the sample rack 200.

FIGS. 18A–C are section views down the middle of a slot 204 of a sample rack 33 showing installation and compression in use, holding a test sample container 34, of a spring 206. At the rear of each slot 204 are top and bottom lipped spring retaining grooves 203 and 205 respectively. The grooves are formed by ridges 207 that are formed on each side of the slot 204 creating two grooves 203 and 205. The springs 206 have rolled ends 208 which aid in retaining the spring in the rack by slipping over the tips of grooves 203 and 205. The normal unstressed position of the spring 206 is shown in FIG. 18A. The bottom end 208 fails to reach grooves 205 until this spring is extended during installation so that lower rolled end 208 falls into grooves 205. Upon insertion of a sample tube as shown in FIG. 18C, spring 206 is stressed further under a force 211 extending the bottom end 208 downward into a slack accommodation extension 213 of groove 205. Upon tube removal spring 206 returns to the state of FIG. 18B.

The test tube 214 has affixed thereto a bar code label 216. A portion of the test tube 214 to which the bar code label is attached is exposed through the slot 204a and thus visible to the reader 83.

While the sample racks can hold test tubes having a range of diameters, it should also be noted that within this range it is preferable to place test tubes having similar diameters in the same sample rack. Thus, and as will be described further below, while each sample rack can hold test tubes having a diameter in the range of 10.25–16.5 mm it may be desirable to designate particular racks to hold test tubes having diameters within a particular range.

It should also be noted that although in this particular embodiment the openings 202a–202e are provided having a circular cross sectional shape, other cross sectional shapes may also be used. For example, the opening may be provided having a rectangular, square, triangular or any other cross-sectional shape. Also the opening may be provided having tapered walls to thus more easily hold cone-shaped vessels. The particular shape of the opening should be selected such that the sample-containing vessel disposed therein can be easily placed into and removed from the sample rack 200. Furthermore, the openings 202a–202e need not all have the same shape. Regardless of the size and shape of the openings, the spring arrangement described above can be employed to secure and firmly hold the sample-containing vessels therein.

Referring again to FIGS. 10–17, the front end of the sample rack has load slot 152 formed therein. The load slot 152 accepts the load guide 150, (FIGS. 7 and 9 respectively) to thus properly align the sample rack 200 in the load position of the input queue.

Figure 2:
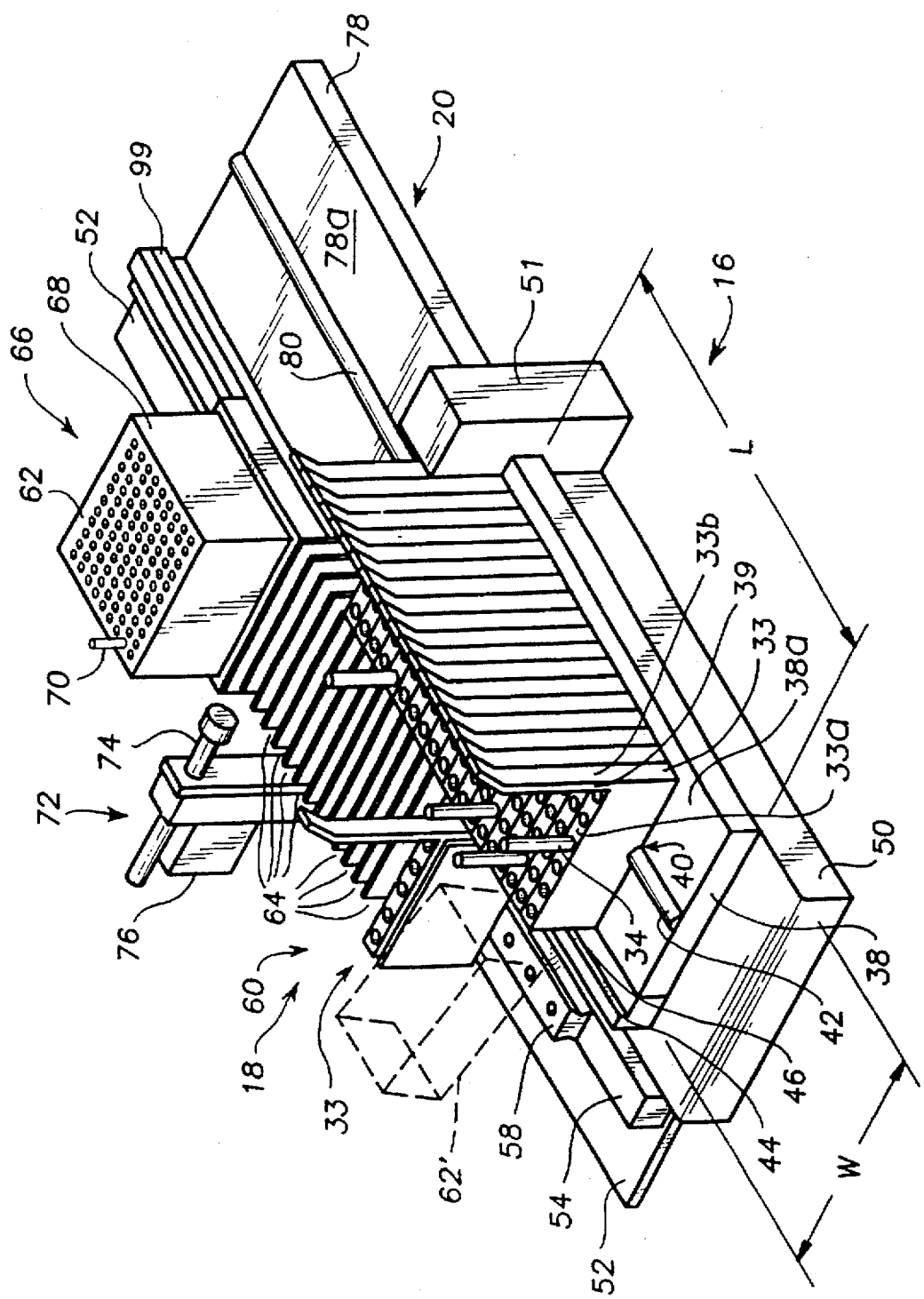
FIG. 2 is a perspective view of a sample transport system having an input queue and a process queue and an output queue.

Similarly, the back end of the sample rack 200 has opening 46 which mates with the input queue edge guide 48 (FIGS. 2, 3) and exit queue edge guide 99 (FIGS. 2, 3). The opening 46 includes a raised portion 222 which engages a corresponding shape on the input queue guide 48 which assists in locating the sample rack 200 on the input queue and prevents the rack 200 from tipping over or sliding off of the input queue.

As described above in conjunction with FIG. 9, however, the back edge guide 99 is provided as an L-shaped member. The guide 99 thus mates only with a front portion 46a of the opening 46 such that the racks may be easily removed from the exit queue.

The sample rack 200 also includes a handle 224 with which a user may carry the sample rack 200. A top angled portion of the handle has a depression 226 formed therein to lend an ergonomic design which is comfortable for a user to grasp.

The handle 224 also has a side surface 228 on which may be attached a vertical bar code label 229. The vertical bar code label 229 has a plurality of barcodes disposed thereon. The barcodes identify the size (e.g. diameter range) of test tubes which are accommodated in the sample rack 200. A sliding clip 233 is disposed around the handle 224 of the sample rack 200 and a user arranges the clip 233 to indicate the size of test tube actually disposed in the sample rack 200. A further barcode region 230 identifies the sample rack serial number. Thus each individual sample rack has its own unique identifying number.

In operation, when the sample rack 200 is moved from the input queue to the process queue the barcode reader reads the barcode on label 228 which are either not blocked by or are emphasized by the sliding clip 233. Thus the barcode reader can identify the type (i.e. the size) of the test tube disposed in the sample rack 200. As mentioned above the sample rack 200 is able to hold test tubes having different diameters and shapes. However, to improve alignment at the sample probe with the opening of the test tube, the system controller preferably knows the type of the test tube.

Figure 11:
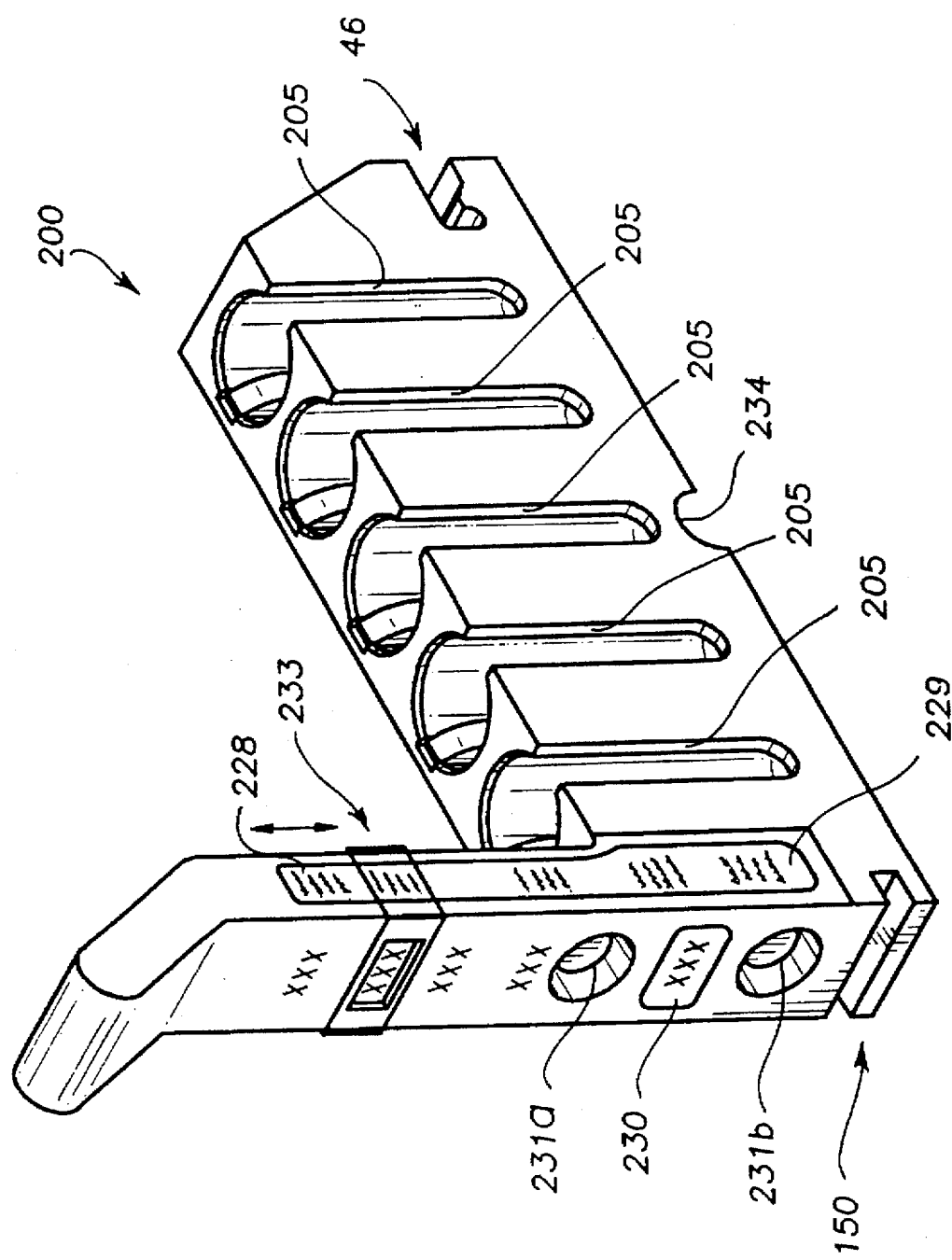

The entire sample rack 200 including handle 224 may be provided as a single piece via injection molding techniques. Alternatively, the test tube carrying portion of the sample rack 200 and the handle 224 may be provided as separate pieces and mated together via screws, epoxy, or any other fastening technique well known to those of ordinary skill in the art. Thus as shown in FIG. 11, a pair of screws in holes 231a, 231b secure the handle 224 to the base portion of the sample rack 200 via screws 231c, not shown.

Figure 12:
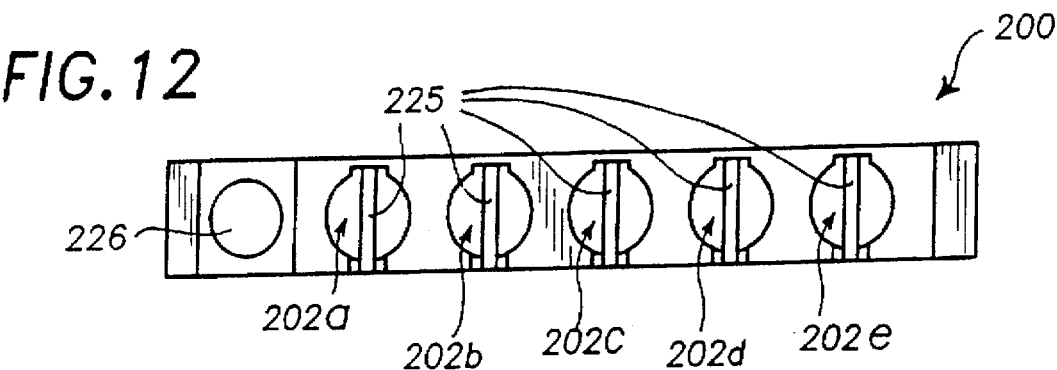
FIG. 12 is a top view of a sample rack.

As may be clearly seen in FIG. 12, each of the holes 202 may optionally be provided with slots 225 formed in the bottom thereof to stabilize the test tube in the holes 202.

The bottom surface of the sample rack 200 has a grove 234 formed therein which mates with and accommodates the guides 42, 80 (FIG. 2) of the input and exit queues.

Figure 13:
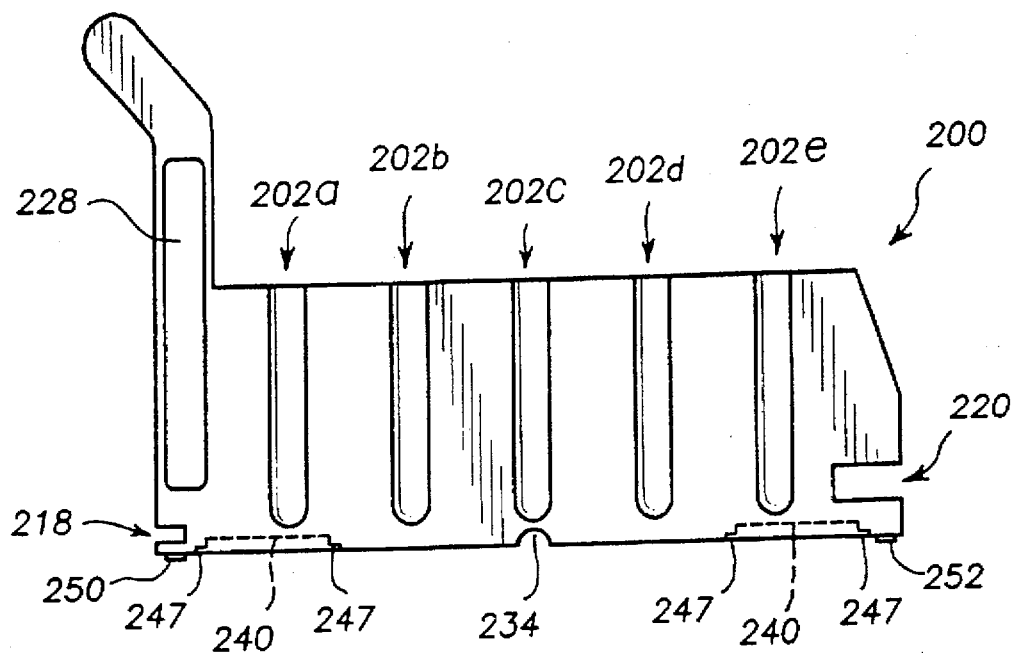
FIG. 13 is a is a side view of a sample rack.

The bottom surface of the sample rack 200 also has formed therein a pair of rectangular shaped cavities 240 (FIG. 13). A magnetically attractive member 244 (FIG. 15) is disposed in each of the cavities 240. The magnetically attractive member may be molded into the bottom surface of the sample rack. Similarly a cover 246 may likewise be fastened to the sample rack over member 244. The members 244 are symmetrically disposed about a latitudinal center line 245 of the sample rack 200.

In this particular embodiment, each of the magnetically attractive members 244 is provided as a magnetically attractive stainless steel plate having a generally rectangular shape. As may be more clearly seen in FIG. 15, a first portion 244c of the bottom surface is slightly recessed from (or substantially aligned with) the bottom surface of the sample rack 200. A second portion 244b of the plate 244 angles into the rack 200 body as discussed above.

As described above in conjunction with FIG. 6, in operation a magnet assembly 121 approaches the sample rack from a direction such that the magnet first attracts the angled second portion 244b of the member 244. Thus, the force of the magnetic field provided from the magnet assembly 120 (FIG. 6) is gradually introduced to the member 244.

Figure 14:
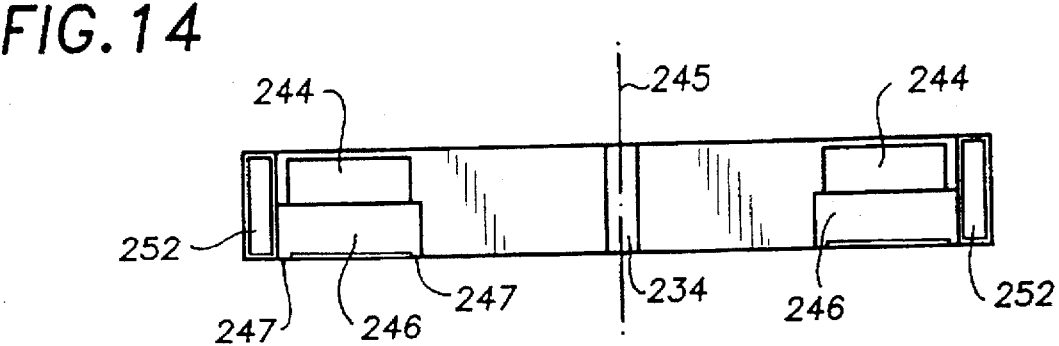
FIG. 14 is a bottom view of a sample rack.
Figure 19:
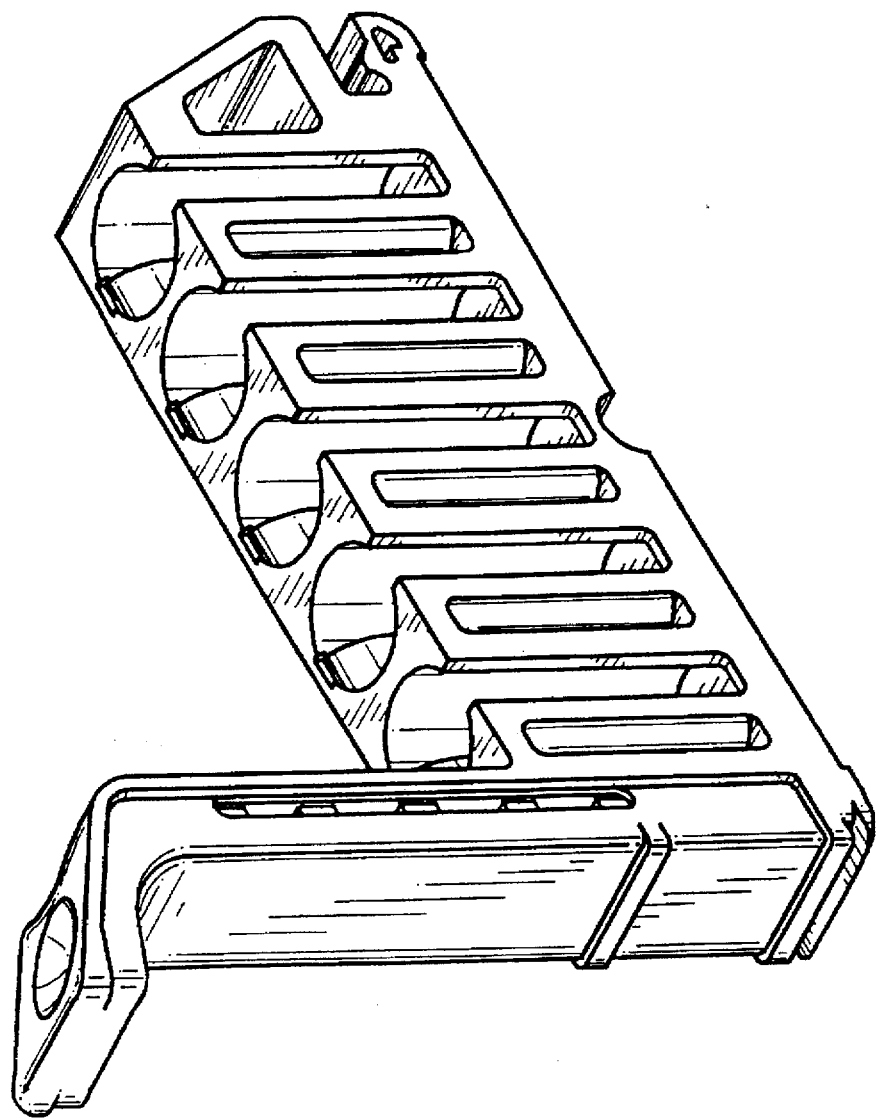
FIG. 19 is a front perspective view of a design for a sample rack according to the invention.
Figure 20:
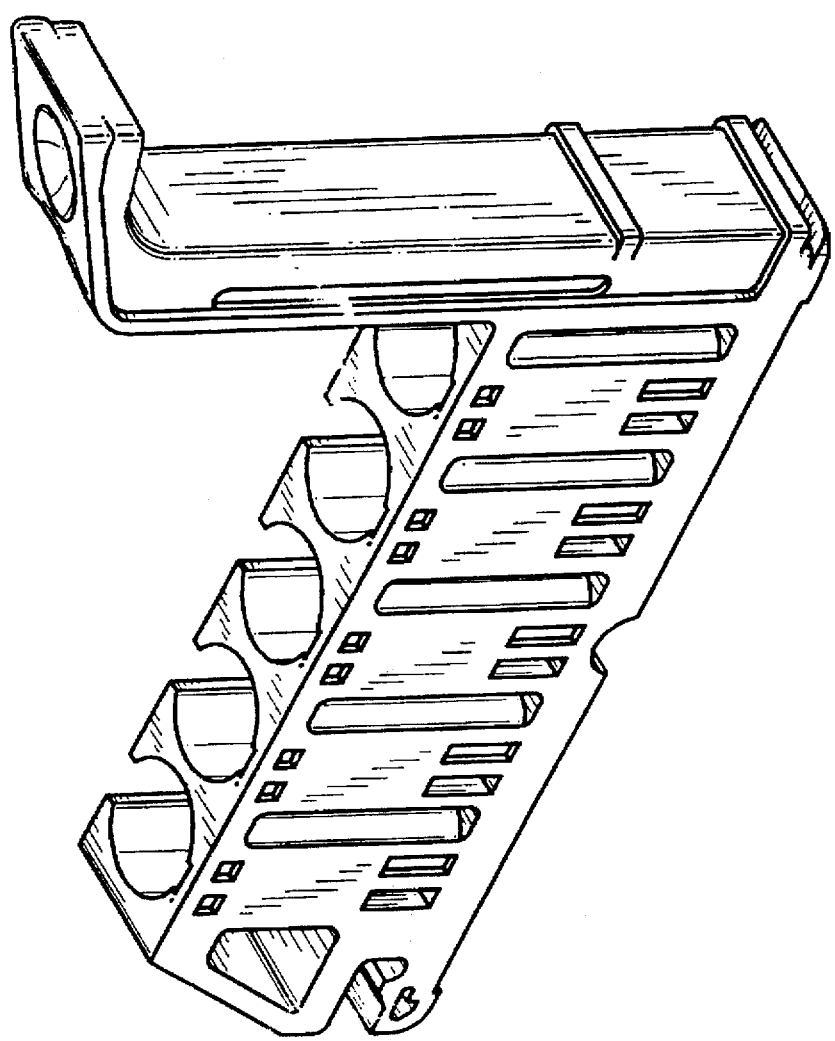
FIG. 20 is a rear perspective view of a design for a sample rack according to the invention.
Figure 22:
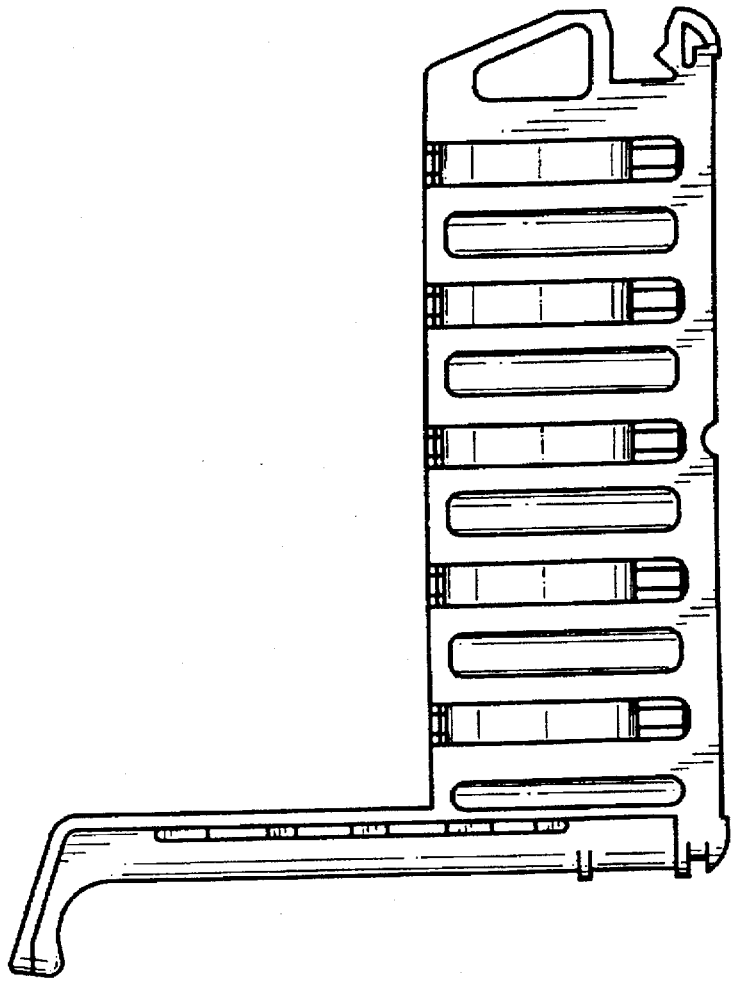
FIG. 22 is a front elevational view of a design for a sample rack according to the invention.
Figure 21:
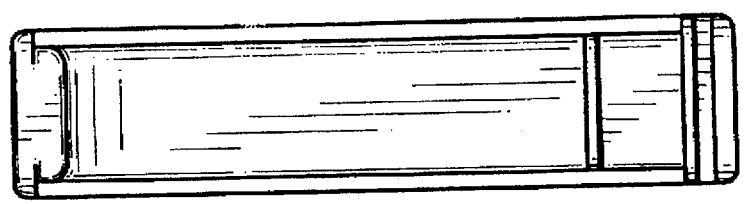
FIG. 21 is front side elevational view of a design for a sample rack according to the invention.
Figure 24:
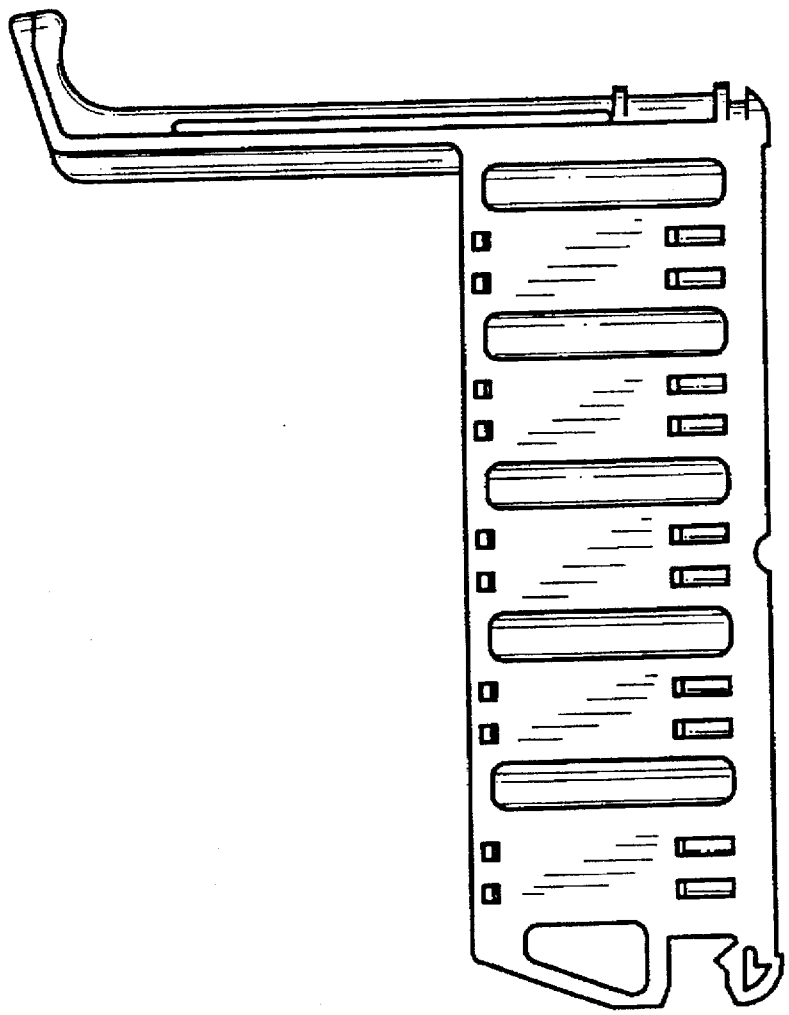
FIG. 24 is a back side elevational view of a design for a sample rack according to the invention.
Figure 23:
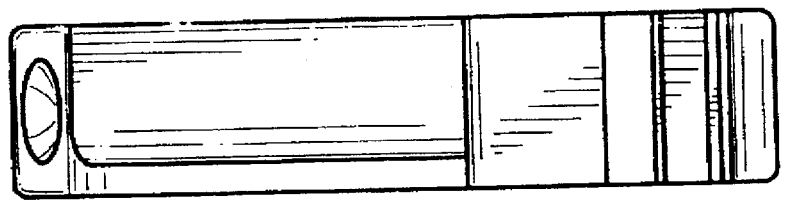
FIG. 23 is a rear side elevational view of a design for a sample rack according to the invention.
Figure 25:
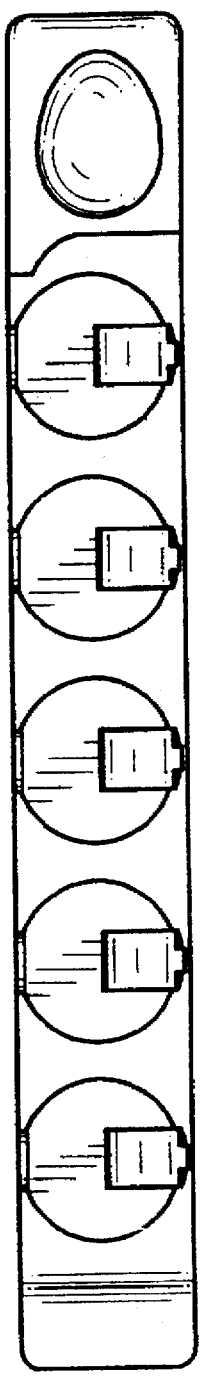
FIG. 25 is a top view of a design for a sample rack according to the invention.
Figure 26:
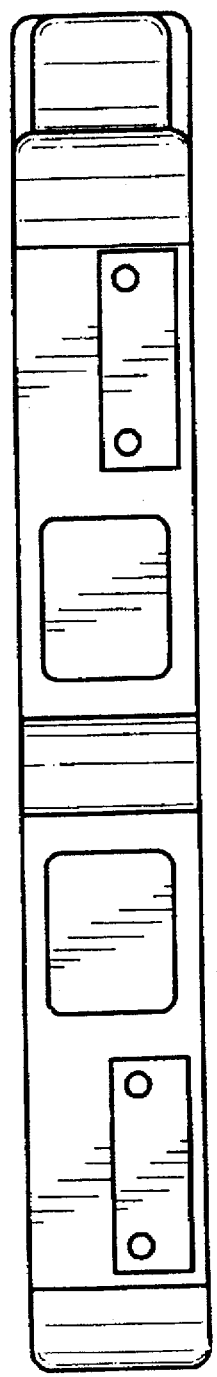
FIG. 26 is a bottom view of a design for a sample rack according to the invention.
Figure 27:
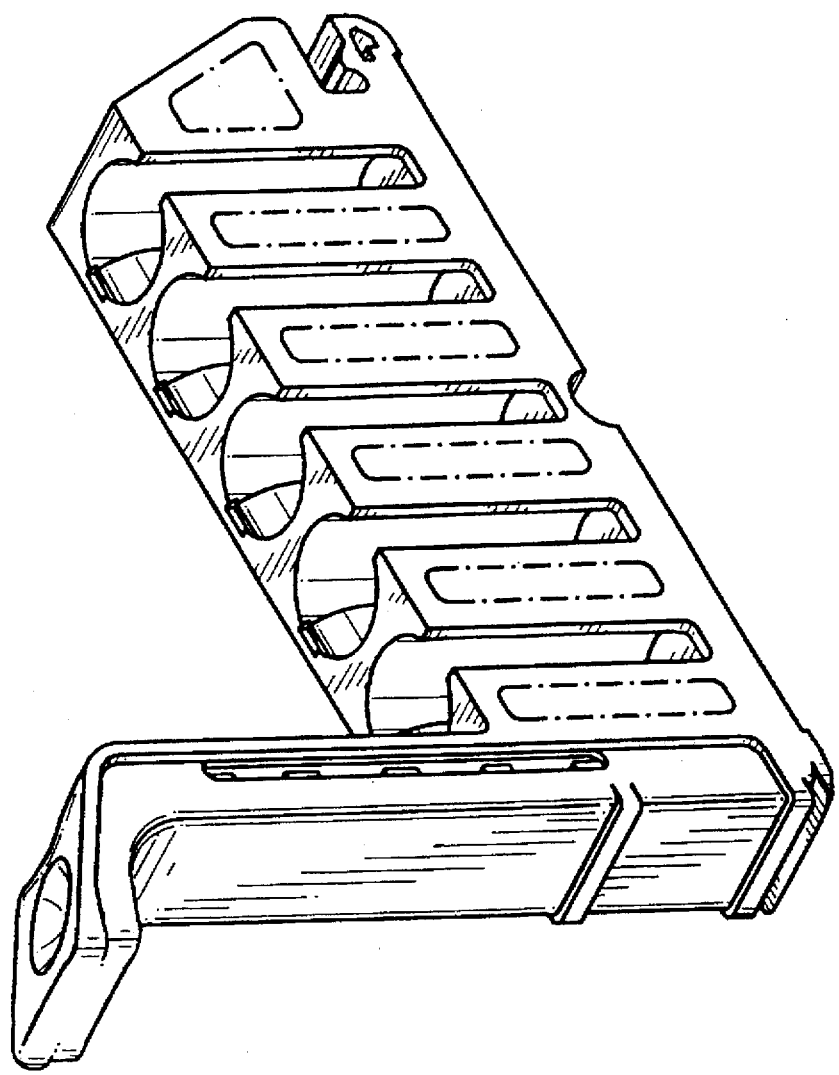
FIG. 27 is a front perspective view of an alternative design for a sample rack according to the invention.
Figure 28:
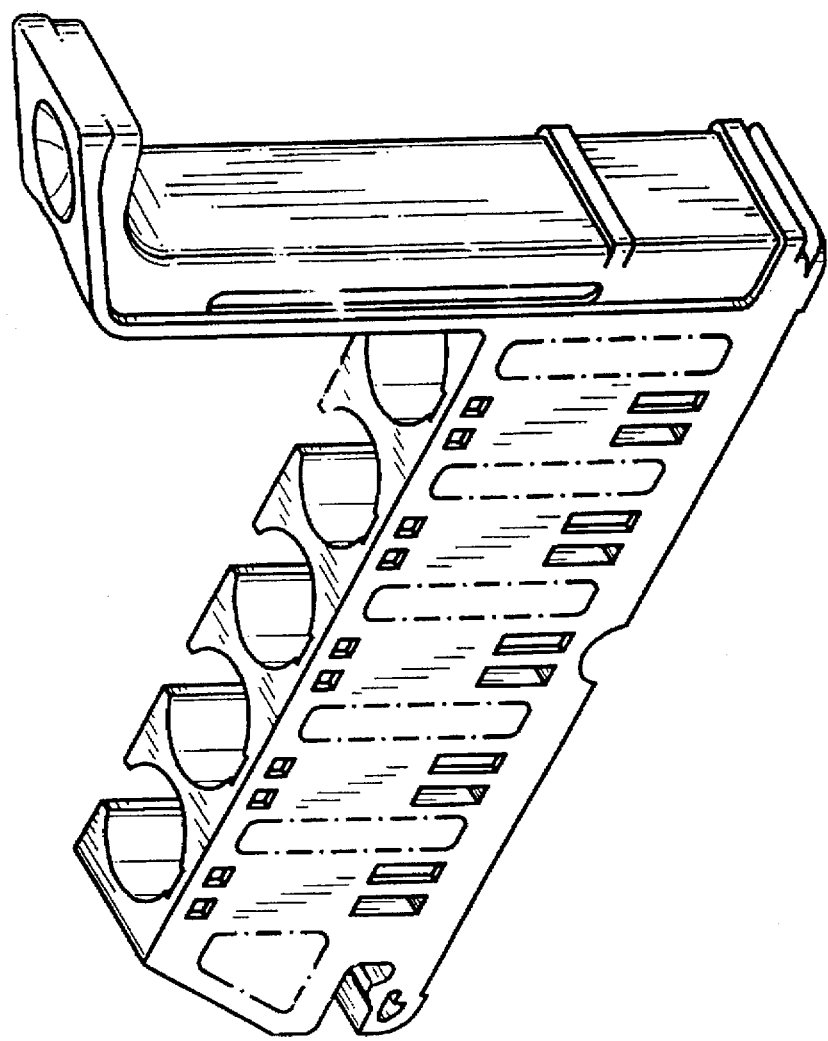
FIG. 28 is a rear perspective view of an alternative design for a sample rack according to the invention.
Figure 29:
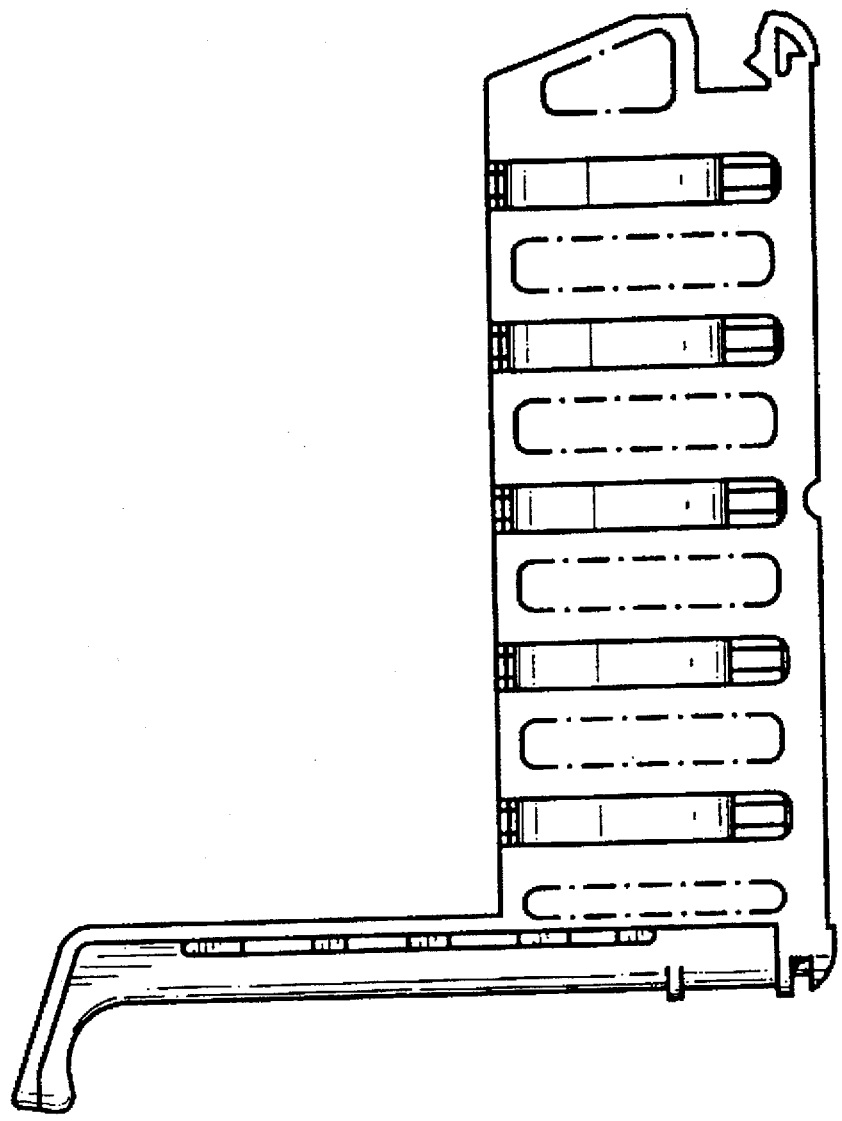
FIG. 29 is front side elevational view of an alternative design for a sample rack according to the invention.
Figure 30:
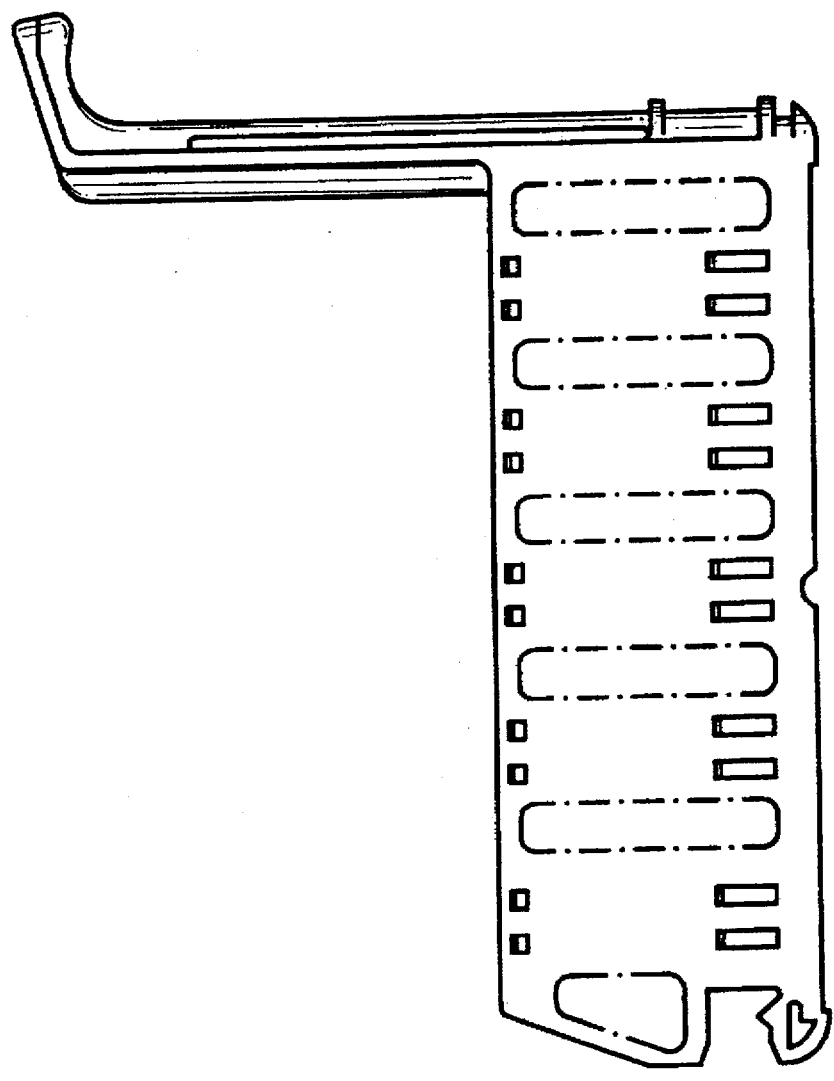
FIG. 30 is a back side elevational view of an alternative design for a sample rack according to the invention.
Figure 31:
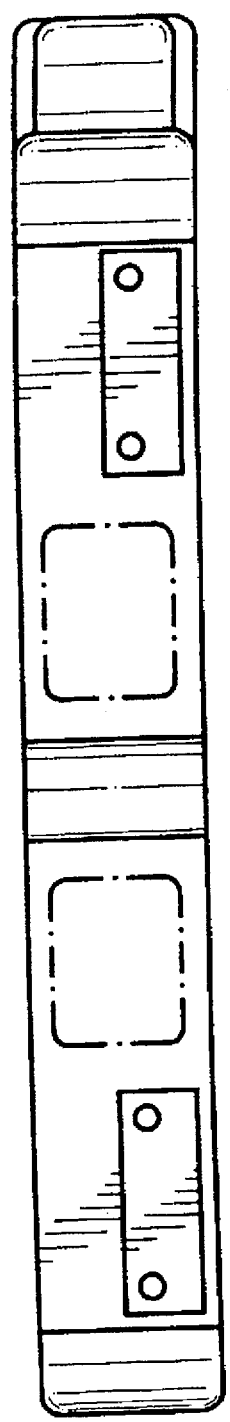
FIG. 31 is a bottom view of an alternative design for a sample rack according to the invention.

A pair of covers 246 are disposed over the openings 240. The covers 246 fit into grooves 247 (FIG. 15) formed proximate the openings 240. The covers 246 are selected to have a size and shape such that the cover 246 forms a snap fit in the openings 240 to thus secure the plates 244 in the rack 200 while leaving exposed at least a portion of the member 244 (FIG. 14).

It should be noted that in this particular embodiment, the sample rack members 244, are spaced apart and positioned in the bottom surface of the sample rack 200 such that when the sample rack 200 is placed on a tray of a conveyor system such as the conveyor system of FIG. 8, the magnet assemblies 173, (FIG. 8) coupled to the belts 170a, 170b (FIG. 8) pass directly under the members 244.

Projecting from a bottom surface of the sample rack 200 are a pair of raised portions or rails 250, 252. The rails 250, 252 space the bottom surface of the sample rack along with member 244 from the queue surface and thus the member 244 from a surface on which the racks are placed. Thus, the rails 250, 252 decrease the surface area of the sample rack 200 which contacts, for example, the surface of the tray 114 (FIGS. 5, 6) on which the rack 200 is placed. Consequently frictional forces between the sample rack 200 and the tray 38 are reduced. This results in a lower magnetic force being required to move sample racks 200 along the tray 38.

Having described preferred embodiments of the invention, it will now become apparent to one of skill in the art that other embodiments incorporating the concepts may be used.

For example, the drive system could be provided having a single belt and magnet coupled thereto. The belt and magnet would preferably be disposed along a central longitudinal axis of a transport tray. In such a case the sample rack would include a single magnetically attractive region disposed in the center of the sample rack and aligned with the single belt and magnet when the sample rack is placed on the transport tray. In this case it may be preferable to provide the tray having a pair of guides projecting therefrom with the guides spaced to prevent the sample rack from pivoting about the point to which the single magnet is coupled.

Furthermore, rather than providing a plate for member 244 having a bend therein in the bottom of the sample rack, the plate could be provided having different thicknesses on each end. For example, a first end of the plate could be relatively thin and a second end of the plate could be relatively thick. A magnet coupled to a drive system would first encounter the thin end of the plate. This would result in a relatively weak magnetic coupling. The magnet would then engage the thick end of the plate with a relatively strong force. With this arrangement, the sample rack would smoothly transition from a stationary state to a moving state.

These embodiments are not to be limited to disclosed embodiments but rather should be limited only by the spirit and scope of the appended claims.

What is claimed is:

1. A sample transport system for moving a sample rack having a magnetically attractive region, the transport system comprising:

a drive system comprising
  first and second pulleys spaced by a predetermined distance,
  at least one belt disposed about said first and second pulleys, and
  a motor coupled to at least one of said first and second pulleys, said motor adapted for moving said belt in first and second opposite directions;

at least one magnet coupled to said at least one belt of said drive system for motion of said at least one magnet by said drive system;

a stationary tray having a first end, a second end and a first surface adapted to receive the sample rack; wherein the first surface of said tray is disposed proximate and spaced a predetermined distance from a first surface of said magnet such that a magnetic force provided by said magnet is present above the first surface of said tray and enables movement of said sample rack in a generally linear direction across said tray with motion of said magnet;

a housing in which said magnet is disposed, said housing for securing said magnet coupled to said belt through a profile on said belt attached to one end of the housing for extending the motion of the magnet under the first surface of said tray beyond said at least one pulley to enable movement of said sample rack in a generally linear direction across said tray to an end point, a first end of said tray defining a load station at said end point to which a sample rack is adapted to be moved by said at least one magnet; and a controller for causing said at least one magnet to move a sample rack located adjacent said load station away from a sample rack located in said load station to permit relative motion between said sample racks.

2. The sample transport system of claim 1 wherein the first surface of said tray is disposed over the first surface of said magnet.

3. The sample transport system of claim 1 further comprising a sensor disposed proximate the second end of said tray for detecting when the sample rack has reached the second end of said tray.

4. The transport system of claim 1 wherein two belts are positioned adjacent said tray, each belt having plural magnets and associated housings aligned side by side and magnetically coupled by a path of magnetic susceptibility.

5. The transport system of claim 1 wherein the first surface of said tray is provided having a guide disposed thereon, said guide having a shape selected to engage the sample rack.

6. A sample rack for holding a specimen sample container, the sample rack comprising:

a unitary base having a top surface, a bottom surface including a recess, a first end, a second end, a first side and a second side;

the top surface of said unitary base including a plurality of openings each adapted to hold the specimen sample container;

a magnetically attractive member disposed in the recess of the bottom surface of said base, said magnetically attractive member selected from the group consisting of:

a magnetically attractable metal plate having a first end and a second end wherein the second end of said plate forms an angle with respect to a plane defined by at least a portion of the bottom surface of said base, and a magnetically attractable metal plate having a first end and a second end wherein the second end of said plate is provided having a thickness which is less than the thickness of the first end of said metal plate; and means for securing the specimen sample container within one of the plurality of openings.

7. The rack of claim 6 wherein said base comprises:

a first sidewall projecting from the first side of said base;

a second sidewall projecting from a second side of said base wherein the second sidewall is provided having an aperture provided therein;

a plurality of cross walls coupled between said first and second sidewalls defining the plurality of openings adapted to hold a specimen sample container.

8. The sample rack of claim 7 wherein said means comprises:

a spring coupled to the first one of said first sidewall, said second sidewall and said plurality of cross walls, such that when the specimen sample container is disposed in one of the plurality of openings, said spring contacts a first surface of the sample specimen container and urges a second surface of the sample specimen container against one of said first sidewall, said second sidewall and said plurality of cross walls which define the opening.

9. The sample rack of claim 6 wherein said magnetically attractive member is provided as a magnet.

10. The sample rack of claim 6 wherein the bottom surface of said base has first and second rails projecting therefrom.

11. The sample rack of claim 6 further comprising a pin for indicating to a sensor when the rack has reached the sensor.

12. The sample rack of claim 6 wherein said means comprises a slot provided in a surface of said base in one of the plurality of openings.

13. The sample rack of claim 6 wherein the bottom surface of said base is provided having a second plurality of openings therein, at least one of said openings having a magnetically attractive member disposed therein.

14. A sample transport system for moving a sample rack having a magnetically attractive region, the transport system comprising:

a drive system comprising:

first and second pulleys spaced by a predetermined distance;

at least one belt disposed about said first and second pulleys; and a motor coupled to at least one of said first and second pulleys, said motor adapted for moving said belt in first and second opposite directions;

at least one magnet coupled to said at least one belt of said drive system for motion of said at least one magnet by said drive system;

a tray having a first end, a second end and a first surface adapted to receive the sample rack wherein the first surface of said tray is disposed proximate and spaced a predetermined distance from a first surface of said magnet such that a magnetic force provided by said magnet is present above the first surface of said tray and which magnetic force moves across said tray with motion of said magnet;

a housing in which said magnet is disposed, said housing for securing said magnet coupled to said belt through a profile on said belt attached to one end of the housing for increasing the motion of the magnet under the first surface of said tray beyond said at least one pulley to move said sample rack on said tray to and end point;

an end of said tray defining a load station at said end point to which a sample rack is adapted to be moved by said at least one magnet; and a controller for causing said at least one magnet to move a sample rack adjacent said load station away from a sample rack in said load station to permit relative motion between said sample racks.

15. A sample rack for holding a specimen sample container, the sample rack comprising:

a base having a top surface, a bottom surface including a recess, a first end, a second end, a first side and a second side;

a magnetically attractable metal plate disposed in the recess in the bottom surface of said base, said metal plate having a first end and a second end wherein the second end of said plate is provided having a shape such that the second end of said plate forms an angle with respect to a plane defined by at least a portion of the bottom surface of said base; and means for coupling the specimen sample container to said base.

16. A sample rack for holding a specimen sample container, the sample rack comprising:

a base having a top surface, a bottom surface having a recess, a first end, a second end, a first side and a second side;

a magnetically attractive member disposed in the recess of the bottom surface of said base wherein said magnetically attractive member is provided as a magnetically attractable metal plate having a first end and a second end wherein the second end of said plate is provided having a thickness which is less than the thickness of the first end of said metal plate; and means for coupling the specimen sample container to said base.

* * * * *